US007919263B2

(12) United States Patent
Shiotsuka et al.

(10) Patent No.: US 7,919,263 B2
(45) Date of Patent: Apr. 5, 2011

(54) ORGANIC MATERIAL-IMMOBILING STRUCTURE AND METHOD FOR PRODUCTION OF THE SAME, AND PEPTIDE AND DNA THEREFOR

(75) Inventors: Hidenori Shiotsuka, Ebina (JP); Takeshi Imamura, Chigasaki (JP); Tsuyoshi Nomoto, Komae (JP); Miki Ogawa, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 773 days.

(21) Appl. No.: 10/548,442

(22) PCT Filed: Aug. 18, 2004

(86) PCT No.: PCT/JP2004/012153
§ 371 (c)(1),
(2), (4) Date: Mar. 14, 2008

(87) PCT Pub. No.: WO2005/016971
PCT Pub. Date: Feb. 24, 2005

(65) Prior Publication Data
US 2010/0216253 A1    Aug. 26, 2010

(30) Foreign Application Priority Data

Aug. 19, 2003 (JP) ................................ 2003-295476
Jul. 28, 2004 (JP) ................................ 2004-220170

(51) Int. Cl.
*G01N 31/00* (2006.01)
*G01N 33/53* (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

U.S. PATENT DOCUMENTS

| | | | |
|---|---|---|---|
| 5,653,675 A | 8/1997 | Kanno et al. ................. 588/249 |
| 5,665,597 A | 9/1997 | Imamura et al. ........... 435/253.3 |
| 5,679,568 A | 10/1997 | Imamura et al. ........... 435/262.5 |
| 5,693,527 A | 12/1997 | Imamura ....................... 435/262 |
| 5,803,664 A | 9/1998 | Kawabata et al. ............ 405/128 |
| 5,807,736 A | 9/1998 | Kozaki et al. ............. 435/262.5 |
| 5,854,059 A | 12/1998 | Kozaki et al. ................. 435/262 |
| 5,863,789 A | 1/1999 | Komatsu et al. .............. 435/262 |
| 5,945,331 A | 8/1999 | Kozaki et al. ................. 435/262 |
| 5,962,305 A | 10/1999 | Mihara et al. ............. 435/262.5 |
| 5,993,658 A | 11/1999 | Kato et al. .................... 210/611 |
| 6,004,772 A | 12/1999 | Imamura et al. ............... 435/34 |
| 6,017,746 A | 1/2000 | Imamura et al. ........... 435/252.1 |
| 6,096,530 A | 8/2000 | Kato et al. ................. 435/253.3 |
| 6,319,706 B1 | 11/2001 | Kawaguchi et al. ....... 435/293.1 |
| 6,424,418 B2 | 7/2002 | Kawabata et al. ............ 356/445 |
| 6,472,191 B1 | 10/2002 | Yano et al. .................... 435/189 |
| 6,479,621 B2 | 11/2002 | Honma et al. ................. 528/361 |
| 6,586,562 B2 | 7/2003 | Honma et al. ................. 528/361 |
| 6,649,381 B1 | 11/2003 | Honma et al. ................. 435/135 |
| 6,660,516 B1 | 12/2003 | Imamura et al. ........... 435/252.8 |
| 6,686,439 B2 | 2/2004 | Kenmoku et al. ............. 528/272 |
| 6,803,444 B2 | 10/2004 | Suzuki et al. ................. 528/361 |
| 6,808,854 B2 | 10/2004 | Imamura et al. .............. 430/110 |
| 6,828,074 B2 | 12/2004 | Yano et al. ................. 430/109.1 |
| 6,846,681 B2 | 1/2005 | Buriak et al. .................. 436/527 |
| 6,853,477 B2 | 2/2005 | Nomoto et al. ............... 359/296 |
| 6,855,472 B2 | 2/2005 | Imamura et al. ........... 430/109.4 |
| 6,858,367 B2 | 2/2005 | Yano et al. .................... 430/109 |
| 6,858,417 B2 | 2/2005 | Yano et al. .................... 435/189 |
| 6,861,496 B2 | 3/2005 | Kenmoku et al. ............. 528/272 |
| 6,861,550 B2 | 3/2005 | Honma et al. .................. 560/53 |
| 6,864,074 B2 | 3/2005 | Yano et al. .................... 435/189 |
| 6,867,023 B2 | 3/2005 | Honma et al. ................. 435/135 |
| 6,869,782 B2 | 3/2005 | Kenmoku et al. ............. 435/130 |
| 6,908,720 B2 | 6/2005 | Kenmoku et al. ............... 430/97 |
| 6,916,861 B2 | 7/2005 | Nomoto et al. ............... 523/160 |
| 6,951,745 B2 | 10/2005 | Nomoto et al. ............... 435/118 |
| 7,153,622 B2 | 12/2006 | Honma et al. ................. 430/105 |
| 2003/0170716 A1 | 9/2003 | Yano et al. ........................ 435/6 |
| 2003/0194443 A1 | 10/2003 | Yano et al. .................... 424/497 |
| 2004/0005638 A1 | 1/2004 | Honma et al. ................. 435/7.1 |
| 2004/0067576 A1 | 4/2004 | Honma et al. ........... 435/252.34 |
| 2005/0208635 A1 | 9/2005 | Nomoto et al. ............... 435/135 |
| 2006/0115861 A1 | 6/2006 | Shiotsuka et al. ............. 435/7.9 |
| 2006/0172398 A1 | 8/2006 | Nomoto et al. ............... 435/135 |
| 2006/0172399 A1 | 8/2006 | Nomoto et al. ............... 435/135 |
| 2006/0172400 A1 | 8/2006 | Nomoto et al. ............... 435/135 |
| 2006/0183235 A1 | 8/2006 | Hashimoto et al. ............. 436/86 |

FOREIGN PATENT DOCUMENTS

| | | |
|---|---|---|
| DE | 202 00 847 | 10/2002 |
| JP | 6-3317 | 1/1994 |
| JP | 2000-139459 | 5/2000 |
| JP | 2001-46100 | 2/2001 |
| JP | 2001-128672 | 5/2001 |

(Continued)

OTHER PUBLICATIONS

Andrew Bradbury, et al., "Use of Living Columns to Select Specific Phage Antibodies", Bio/Technology, vol. 11, Dec. 1993, pp. 1565-1569.

Lawrence L. Brott, et al., "Ultrafast holographic nanopatterning of biocatalytically formed silica", Nature, XP-002975722, vol. 413, Sep. 20, 2001, pp. 291-293.

(Continued)

*Primary Examiner* — Lisa V Cook
(74) *Attorney, Agent, or Firm* — Fitzpatrick, Cella, Harper & Scinto

(57) ABSTRACT

The invention provides an organic material-immobilizing structure employing new immobilization means, characterized in that at least a part of the surface of the substrate is comprised of one or more members containing silicon oxide, the organic material is bound to the surface of the substrate through a binding domain bound to the organic material and containing an amino acid sequence capable of binding to silicon oxide, selected from the group consisting of amino acid sequences of SEQ ID NOS: 1 and 2: Val-Ser-Pro-Met-Arg-Ser-Ala-Thr-Thr-His-Thr-Val; and Ile-Pro-Met-His-Val-His-His-Lys-His-Pro-His-Val, and derivatives thereof.

10 Claims, 1 Drawing Sheet

FOREIGN PATENT DOCUMENTS

| | | |
|---|---|---|
| JP | 2001-178457 | 7/2001 |
| JP | 2002-95471 | 4/2002 |
| WO | 99/37705 A1 | 7/1999 |
| WO | 02/19407 | 3/2002 |

OTHER PUBLICATIONS

Alain Charbit, et al., "Versatility of a vector for expressing foreign polypeptides at the surface of Gram-negative bacteria", Gene, vol. 70, 1988, pp. 181-189.

Steven E. Cwirla, et al., "Peptides on phage: A vast library of peptides for identifying ligands", Proceedings of the National Academy of Sciences, vol. 87, Aug. 1990, pp. 6378-6382.

J. F. Diaz, et al., Journal of Molecular Catalysis B: Enzymatic 2, 1996, pp. 115-126.

Joseph A. Francisco, et al., "Production and fluorescence-activated cell sorting of *Escherichia coli* expressing a functional antibody fragment on the external surface", Proceedings of the National Academy of Sciences, vol. 90, Nov. 1993, pp. 10444-10448.

Patrick Fuchs, et al., "Targeting Recombinant Antibodies to the Surface of *Escherichia coli*: Fusion to a Peptidoglycan Associated Lipoprotein", Bio/Technology, vol. 9, Dec. 1991, pp. 1369-1372.

P. J. Halling, et al., "Magnetic supports for immobilized enzymes and bioaffinity adsorbents", Enzyme Microb. Technol., vol. 2, Jan. 1980, pp. 2-10.

Lisbeth Hedegaard, et al., "Type 1 fimbriae of *Escherichia coli* as carriers of heterologous antigenic sequences", Gene, vol. 85, 1989, pp. 115-124.

A. Nyamsi Hendji, et al., "Covalent immobilization of glucose oxidase on silanized platinum microelectrode for the monitoring of glucose", Sensors and Actuators B: vol. 15-16, 1993, pp. 127-134.

Maurice Hofnung, "Expression of Foreign Polypeptides at the *Escherichia coli* Cell Surface", Methods in Cell Biology, vol. 34, 1991, pp. 77-105.

Thomas Klauser, et al., "Extracellular transport of cholera toxin B subunit using *Neisseria* IgA protease β-domain: conformation-dependent outer membrane translocation", EMBO Journal, vol. 9, 1990, pp. 1991-1999.

Rajesh R. Naik, et al., "Silica-Precipitating Peptides Isolated from a Combinatorial Phage Display Peptide Library", Journal of Nanoscience and Nanotechnology, XP-002975721,vol. 2, 2002, pp. 95-100.

S. Pistor, et al., "Expression of Viral Hemagglutinin on the Surface of *E. coli*", Klin Wochenschr, vol. 66, 1988, pp. 110-116.

J. Sambrook, et al., Molecular Cloning, A Laboratory Manual, Second Edition, Cold Spring Harbor Laboratory Press, 1989, p. 5.72.

Jamie K. Scott, et al., "Searching for Peptide Ligands with an Epitope Library", Science, vol. 249, 1990, pp. 386-390.

Ping Wang, et al., "Enzyme Stabilization by Covalent Binding in Nanoporous Sol-Gel Glass for Nonaqueous Biocatalysis", Biotechnology and Bioengineering, vol. 74, No. 3, Aug. 5, 2001, pp. 249-255.

Dongyuan Zhao, et al., "Triblock Copolymer Syntheses of Mesoporous Silica with Periodic 50 to 300 Angstrom Pores", Science, vol. 279, Jan. 23, 1998, pp. 548-552.

```
                        SEQUENCE LISTING

<160> NUMBER OF SEQ ID NOS: 36

<210> SEQ ID NO 1
<211> LENGTH: 12
<212> TYPE: PRT
<213> ORGANISM: Artificial
<220> FEATURE:
<223> OTHER INFORMATION: SBA-binding peptide

<400> SEQUENCE: 1

Val Ser Pro Met Arg Ser Ala Thr Thr His Thr Val
1               5                   10

<210> SEQ ID NO 2
<211> LENGTH: 12
<212> TYPE: PRT
<213> ORGANISM: Artificial
<220> FEATURE:
<223> OTHER INFORMATION: SBA-15-binding peptide

<400> SEQUENCE: 2

Ile Pro Met His Val His His Lys His Pro His Val
1               5                   10

<210> SEQ ID NO 3
<211> LENGTH: 58
<212> TYPE: DNA
<213> ORGANISM: Artificial
<220> FEATURE:
<223> OTHER INFORMATION: Coding for peptide of SEQ ID:1

<400> SEQUENCE: 3
gatccgtgag ccccatgagg agcgccacca cccacaccgt gggtggaggt tcggagct      58

<210> SEQ ID NO 4
<211> LENGTH: 48
<212> TYPE: DNA
<213> ORGANISM: Artificial
<220> FEATURE:
<223> OTHER INFORMATION: Complimentary strand for ssDNA of SEQ ID:3
```

```
<400> SEQUENCE: 4
cgaacctcca cccacggtgt gggtggtggc gctcctcatg gggctcac          48

<210> SEQ ID NO 5
<211> LENGTH: 58
<212> TYPE: DNA
<213> ORGANISM: Artificial
<220> FEATURE:
<223> OTHER INFORMATION: Coding strand for peptide of SEQ ID:2

<400> SEQUENCE: 5
gatccatccc catgcacgtg caccacaagc accccccacgt gggtggaggt tcggagct      58

<210> SEQ ID NO 6
<211> LENGTH: 48
<212> TYPE: DNA
<213> ORGANISM: Artificial
<220> FEATURE:
<223> OTHER INFORMATION: Complimentary strand for ssDNA of SEQ ID:5

<400> SEQUENCE: 6
cgaacctcca cccacgtggg ggtgcttgtg gtgcacgtgc atggggat          48

<210> SEQ ID NO 7
<211> LENGTH: 1680
<212> TYPE: DNA
<213> ORGANISM: Pseudomonas cichorii YN2; FERM BP-7375
<220> FEATURE:
<221> NAME/KEY: misc_feature
<222> LOCATION: (1)..(1680)
<223> OTHER INFORMATION: encoding a PHA synthetase

<400> SEQUENCE: 7
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccgggctg caaccgacca gcgatgaccg tcgcttcgcc     240
gatccggcct ggagccagaa cccgctctat aaacgttatt tgcaaaccta cctggcgtgg     300
cgcaaggaac tccacgactg gatcgatgaa agtaacctcg cccccaagga tgtggcgcgt     360
gggcacttcg tgatcaacct catgaccgaa gccatggcgc cgaccaacac cgcggccaac     420
ccggcggcag tcaaacgctt tttcgaaacc ggtggcaaaa gcctgctcga cggcctctcg     480
cacctggcca aggatctggt acacaacggc ggcatgccga ccaggtcaa catgggtgca     540 ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt ttcgacctga gcccggacaa gagcctggcg     720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgatgtc     840
gttaccgcga tcaccggcag caaagacgtg aacatgctcg gcgcctgctc cggcggcatc     900
acttgcaccg cgctgctggg ccattacgcg gcgattggcg aaaacaaggt caacgccctg     960
accttgctgg tgagcgtgct tgataccacc ctcgacagcg atgttgccct gttcgtcaat    1020
gaacagaccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg gtgttcgaca tcctgttctg gaacaacgac    1200
```

| | |
|---|---|
| accacacggt tgcccgcggc gttccacggc gacctgatcg aactgttcaa aaataaccca | 1260 |
| ctgattcgcc cgaatgcact ggaagtgtgc ggcaccccca tcgacctcaa gcaggtgacg | 1320 |
| gccgacatct tttccctggc cggcaccaac gaccacatca ccccgtggaa gtcctgctac | 1380 |
| aagtcggcgc aactgtttgg cggcaacgtt gaattcgtgc tgtcgagcag cgggcatatc | 1440 |
| cagagcatcc tgaacccgcc gggcaatccg aaatcgcgct acatgaccag caccgaagtg | 1500 |
| gcggaaaatg ccgatgaatg gcaagcgaat gccaccaagc ataccgattc ctggtggctg | 1560 |
| cactggcagg cctggcaggc caacgctcg ggcgagctga aaagtcccc gacaaaactg | 1620 |
| ggcagcaagg cgtatccggc aggtgaagcg gcgccaggca cgtacgtgca cgaacggtaa | 1680 |

<210> SEQ ID NO 8
<211> LENGTH: 1683
<212> TYPE: DNA
<213> ORGANISM: Pseudomonas cichorii YN2; FERM BP-7375
<220> FEATURE:
<221> NAME/KEY: misc_feature
<222> LOCATION: (1)..(1683)
<223> OTHER INFORMATION: encoding a PHA synthetase

<400> SEQUENCE: 8

| | |
|---|---|
| atgcgcgata aacctgcgag ggagtcacta cccaccccg ccaagttcat caacgcacaa | 60 |
| agtgcgatta ccggcctgcg tggccgggat ctggtttcga ctttgcgcag tgtcgccgcc | 120 |
| catggcctgc gccaccccgt gcacaccgcg cgacacgcct tgaaactggg tggtcaactg | 180 |
| ggacgcgtgt tgctgggcga caccctgcat cccaccaacc gcaagaccg tcgcttcgac | 240 |
| gatccggcgt ggagtctcaa tccctttat cgtcgcagcc tgcaggcgta cctgagctgg | 300 |
| cagaagcagg tcaagagctg gatcgacgaa agcaacatga gcccggatga ccgcgcccgt | 360 |
| gcgcacttcg cgttcgccct gctcaacgat gccgtgtcgc cgtccaacag cctgctcaat | 420 |
| ccgctggcga tcaaggaaat cttcaactcc ggcggcaaca gcctggtgcg cgggatcggc | 480 |
| catctggtcg atgacctctt gcacaacgat ggcttgcccc ggcaagtcac caggcatgca | 540 |
| ttcgaggttg gcaagaccgt cgccaccacc accggcgccg tggtgtttcg caacgagctg | 600 |
| ctggagctga tccaatacaa gccgatgagc gaaaagcagt attccaaacc gctgctggtg | 660 |
| gtgccgccac agatcaacaa gtactacatt tttgacctca gccccataa cagcttcgtc | 720 |
| cagttcgcgc tcaagaacgg cctgcaaacc ttcgtcatca gctggcgcaa tccggatgta | 780 |
| cgtcaccgcg aatggggcct gtcgacctac gtcgaagcgg tggaagaagc catgaatgtc | 840 |
| tgccgggcaa tcaccggcgc gcgcgaggtc aacctgatgg gcgcctgcgc tggcgggctg | 900 |
| accattgctg ccctgcaggg ccacttgcaa gccaagcgac agctgcgccg cgtctccagc | 960 |
| gcgacgtacc tggtgagcct gctcgacagc caactggaca gcccggccac actcttcgcc | 1020 |
| gacgaacaga ccctggaggc ggccaagcgc cgctcctacc agaaaggtgt gctggaaggc | 1080 |
| cgcgacatgg ccaaggtttt cgcctggatg cgcccaacg atttgatctg gagctacttc | 1140 |
| gtcaacaatt acctgatggg caaggagccg ccggcgttcg acattctcta ctggaacaat | 1200 |
| gacaacacac gcctgccggc cgccctgcat ggtgacttgc tggacttctt caagcacaac | 1260 |
| ccgctgagcc atccgggtgg cctggaagtg tgcggcaccc cgatcgactt gcaaaaggtc | 1320 |
| accgtcgaca gtttcagcgt ggccggcatc aacgatcaca tcacgccgtg ggacgcggtg | 1380 |
| tatcgctcaa ccctgttgct cggtggcgag cgtcgctttg tcctggccaa cagcggtcat | 1440 |
| gtgcagagca ttctcaaccc gccgaacaat ccgaaagcca actacctcga aggtgcaaaa | 1500 |
| ctaagcagcg accccagggc ctggtactac gacgccaagc ccgtcgacgg tagctggtgg | 1560 |

```
acgcaatggc tgggctggat tcaggagcgc tcgggcgcgc aaaaagaaac ccacatggcc    1620
ctcggcaatc agaattatcc accgatggag gcggcgcccg ggacttacgt gcgcgtgcgc    1680
tga                                                                  1683
```

<210> SEQ ID NO 9
<211> LENGTH: 559
<212> TYPE: PRT
<213> ORGANISM: Pseudomonas cichorii YN2; FERM BP-7375
<220> FEATURE:
<221> NAME/KEY: MISC_FEATURE
<222> LOCATION: (1)..(559)
<223> OTHER INFORMATION: PHA synthetase

<400> SEQUENCE: 9

```
Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335
```

```
Leu Phe Val Asn Glu Gln Thr Leu Glu Ala Ala Lys Arg His Ser Tyr
                340                 345                 350

Gln Ala Gly Val Leu Glu Gly Arg Asp Met Ala Lys Val Phe Ala Trp
            355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
                420                 425                 430

Pro Ile Asp Leu Lys Gln Val Thr Ala Asp Ile Phe Ser Leu Ala Gly
            435                 440                 445

Thr Asn Asp His Ile Thr Pro Trp Lys Ser Cys Tyr Lys Ser Ala Gln
            450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
            500                 505                 510

Lys His Thr Asp Ser Trp Trp Leu His Trp Gln Ala Trp Gln Ala Gln
            515                 520                 525

Arg Ser Gly Glu Leu Lys Lys Ser Pro Thr Lys Leu Gly Ser Lys Ala
            530                 535                 540

Tyr Pro Ala Gly Glu Ala Ala Pro Gly Thr Tyr Val His Glu Arg
545                 550                 555

<210> SEQ ID NO 10
<211> LENGTH: 560
<212> TYPE: PRT
<213> ORGANISM: Pseudomonas cichorii YN2; FERM BP-7375
<220> FEATURE:
<221> NAME/KEY: MISC_FEATURE
<222> LOCATION: (1)..(560)
<223> OTHER INFORMATION: PHA synthetase

<400> SEQUENCE: 10

Met Arg Asp Lys Pro Ala Arg Glu Ser Leu Pro Thr Pro Ala Lys Phe
1               5                   10                  15

Ile Asn Ala Gln Ser Ala Ile Thr Gly Leu Arg Gly Arg Asp Leu Val
                20                  25                  30

Ser Thr Leu Arg Ser Val Ala Ala His Gly Leu Arg His Pro Val His
            35                  40                  45

Thr Ala Arg His Ala Leu Lys Leu Gly Gly Gln Leu Gly Arg Val Leu
        50                  55                  60

Leu Gly Asp Thr Leu His Pro Thr Asn Pro Gln Asp Arg Arg Phe Asp
65              70                  75                  80

Asp Pro Ala Trp Ser Leu Asn Pro Phe Tyr Arg Arg Ser Leu Gln Ala
                85                  90                  95

Tyr Leu Ser Trp Gln Lys Gln Val Lys Ser Trp Ile Asp Glu Ser Asn
            100                 105                 110

Met Ser Pro Asp Asp Arg Ala Arg Ala His Phe Ala Phe Ala Leu Leu
        115                 120                 125

Asn Asp Ala Val Ser Pro Ser Asn Ser Leu Leu Asn Pro Leu Ala Ile
    130                 135                 140
```

-continued

```
Lys Glu Ile Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
            165                 170                 175

Thr Arg His Ala Phe Glu Val Gly Lys Thr Val Ala Thr Thr Thr Gly
        180                 185                 190

Ala Val Val Phe Arg Asn Glu Leu Leu Glu Leu Ile Gln Tyr Lys Pro
    195                 200                 205

Met Ser Glu Lys Gln Tyr Ser Lys Pro Leu Leu Val Val Pro Pro Gln
210                 215                 220

Ile Asn Lys Tyr Tyr Ile Phe Asp Leu Ser Pro His Asn Ser Phe Val
225                 230                 235                 240

Gln Phe Ala Leu Lys Asn Gly Leu Gln Thr Phe Val Ile Ser Trp Arg
                245                 250                 255

Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Gly Leu Thr Ile Ala Ala
    290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Thr Leu Phe Ala Asp Glu Gln Thr Leu Glu Ala Ala Lys Arg Arg Ser
            340                 345                 350

Tyr Gln Lys Gly Val Leu Glu Gly Arg Asp Met Ala Lys Val Phe Ala
        355                 360                 365

Trp Met Arg Pro Asn Asp Leu Ile Trp Ser Tyr Phe Val Asn Asn Tyr
    370                 375                 380

Leu Met Gly Lys Glu Pro Pro Ala Phe Asp Ile Leu Tyr Trp Asn Asn
385                 390                 395                 400

Asp Asn Thr Arg Leu Pro Ala Ala Leu His Gly Asp Leu Leu Asp Phe
                405                 410                 415

Phe Lys His Asn Pro Leu Ser His Pro Gly Gly Leu Glu Val Cys Gly
            420                 425                 430

Thr Pro Ile Asp Leu Gln Lys Val Thr Val Asp Ser Phe Ser Val Ala
        435                 440                 445

Gly Ile Asn Asp His Ile Thr Pro Trp Asp Ala Val Tyr Arg Ser Thr
    450                 455                 460

Leu Leu Leu Gly Gly Glu Arg Arg Phe Val Leu Ala Asn Ser Gly His
465                 470                 475                 480

Val Gln Ser Ile Leu Asn Pro Pro Asn Asn Pro Lys Ala Asn Tyr Leu
                485                 490                 495

Glu Gly Ala Lys Leu Ser Ser Asp Pro Arg Ala Trp Tyr Tyr Asp Ala
            500                 505                 510

Lys Pro Val Asp Gly Ser Trp Trp Thr Gln Trp Leu Gly Trp Ile Gln
        515                 520                 525

Glu Arg Ser Gly Ala Gln Lys Glu Thr His Met Ala Leu Gly Asn Gln
    530                 535                 540

Asn Tyr Pro Pro Met Glu Ala Ala Pro Gly Thr Tyr Val Arg Val Arg
545                 550                 555                 560
```

```
<210> SEQ ID NO 11
<211> LENGTH: 20
<212> TYPE: DNA
<213> ORGANISM: Artificial
<220> FEATURE:
<223> OTHER INFORMATION: Primer for PCR amplification

<400> SEQUENCE: 11
tgctggaact gatccagtac                                              20

<210> SEQ ID NO 12
<211> LENGTH: 23
<212> TYPE: DNA
<213> ORGANISM: Artificial
<220> FEATURE:
<223> OTHER INFORMATION: Primer for PCR amplification

<400> SEQUENCE: 12
gggttgagga tgctctggat gtg                                          23

<210> SEQ ID NO 13
<211> LENGTH: 29
<212> TYPE: DNA
<213> ORGANISM: Artificial
<220> FEATURE:
<223> OTHER INFORMATION: Primer for PCR amplification

<400> SEQUENCE: 13
cgagcaagct tgctcctaca ggtgaaggc                                    29

<210> SEQ ID NO 14
<211> LENGTH: 29
<212> TYPE: DNA
<213> ORGANISM: Artificial
<220> FEATURE:
<223> OTHER INFORMATION: Primer for PCR amplification

<400> SEQUENCE: 14
gtattaagct tgaagacgaa ggagtgttg                                    29

<210> SEQ ID NO 15
<211> LENGTH: 29
<212> TYPE: DNA
<213> ORGANISM: Artificial
<220> FEATURE:
<223> OTHER INFORMATION: Primer for PCR amplification

<400> SEQUENCE: 15
ggaccaagct tctcgtctca gggcaatgg                                    29

<210> SEQ ID NO 16
<211> LENGTH: 30
<212> TYPE: DNA
<213> ORGANISM: Artificial
<220> FEATURE:
<223> OTHER INFORMATION: Primer for PCR amplification

<400> SEQUENCE: 16
catccaagct tcttatgatc gggtcatgcc                                   30

<210> SEQ ID NO 17
<211> LENGTH: 45
<212> TYPE: DNA
<213> ORGANISM: Artificial
<220> FEATURE:
<223> OTHER INFORMATION: Primer for PCR amplification
```

-continued

<400> SEQUENCE: 17
agtggatcct ccgagctcag taacaagagt aacgatgagt tgaag          45

<210> SEQ ID NO 18
<211> LENGTH: 45
<212> TYPE: DNA
<213> ORGANISM: Artificial
<220> FEATURE:
<223> OTHER INFORMATION: Primer for PCR amplification

<400> SEQUENCE: 18
atactcgaga ctactagtcc gttcgtgcac gtacgtgcct ggcgc          45

<210> SEQ ID NO 19
<211> LENGTH: 45
<212> TYPE: DNA
<213> ORGANISM: Artificial
<220> FEATURE:
<223> OTHER INFORMATION: Primer for PCR amplification

<400> SEQUENCE: 19
atactcgaga ctactagtgc gcacgcgcac gtaagtcccg ggcgc          45

<210> SEQ ID NO 20
<211> LENGTH: 45
<212> TYPE: DNA
<213> ORGANISM: Artificial
<220> FEATURE:
<223> OTHER INFORMATION: Primer for PCR amplification

<400> SEQUENCE: 20
agtggatcct ccgagctccg cgataaacct gcgagggagt cacta          45

<210> SEQ ID NO 21
<211> LENGTH: 32
<212> TYPE: PRT
<213> ORGANISM: Artificial
<220> FEATURE:
<223> OTHER INFORMATION: SBA-15-binding peptide

<400> SEQUENCE: 21

Val Ser Pro Met Arg Ser Ala Thr Thr His Thr Val Gly Gly Gly Ser
1               5                   10                  15

Gly Gly Gly Ser Ile Pro Met His Val His His Lys His Pro His Val
            20                  25                  30

<210> SEQ ID NO 22
<211> LENGTH: 113
<212> TYPE: DNA
<213> ORGANISM: Artificial
<220> FEATURE:
<223> OTHER INFORMATION: Primer for PCR amplification

<400> SEQUENCE: 22
gatccgtgag ccccatgagg agcgccacca cccacaccgt gcggcggcgg cagcggcggc     60
ggcagcatcc ccatgcacgt gcaccacaag caccccacg tgggagctga gct            113

<210> SEQ ID NO 23
<211> LENGTH: 102
<212> TYPE: DNA
<213> ORGANISM: Artificial
<220> FEATURE:
<223> OTHER INFORMATION: Primer for PCR amplification -continued

```
<400> SEQUENCE: 23
agctcccacg tgggggtgct tgtggtgcac gtgcatgggg atctgccgcc gccgctgccg        60
ccgccgcacg tgtgggtgg tggcgctcct catggggctc ac                          102

<210> SEQ ID NO 24
<211> LENGTH: 108
<212> TYPE: PRT
<213> ORGANISM: Mouse
<220> FEATURE:
<221> NAME/KEY: misc_feature
<223> OTHER INFORMATION: VL_HEL; variable region of light chain of
      antibody to HEL

<400> SEQUENCE: 24

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Thr
        35                  40                  45

Lys Tyr Ala Ser Gln Ser Ile Ser Gly Thr Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Thr Ala
            100                 105

<210> SEQ ID NO 25
<211> LENGTH: 324
<212> TYPE: DNA
<213> ORGANISM: Mouse
<220> FEATURE:
<221> NAME/KEY: misc_feature
<222> LOCATION: (1)..(324)
<223> OTHER INFORMATION: encoding VL_HEL

<400> SEQUENCE: 25
gatatcgtcc tgacccagag cccggcgacc ctctcggtca cccccggcaa ctcggtgtcc        60
ctctcgtgcc gcgcctcgca gtcgatcggc aacaacctcc actggtatca gcagaagtcg       120
cacgagagcc cgcgcctcct gatcaagtac gccagccagt cgatctcggg gatcccgtcg       180
cgcttcagcg gctcgggctc gggcaccgac ttcaccctgt cgatcaacag cgtcgagacg       240
gaggacttcg gcatgtactt ctgccagcag tcgaacagct ggccgtacac cttcggcggc       300
ggtaccaagc tgatcatcac ggcc                                              324

<210> SEQ ID NO 26
<211> LENGTH: 112
<212> TYPE: PRT
<213> ORGANISM: Mouse
<220> FEATURE:
<221> NAME/KEY: misc_feature
<223> OTHER INFORMATION: VH_HEL; variable region of heavy chain of
      antibody to HEL

<400> SEQUENCE: 26

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Thr Thr Ser Asp
            20                  25                  30
```

```
Tyr Trp Ser Trp Ile Arg Lys Phe Pro Gly Asn Arg Leu Glu Tyr Met
            35                  40                  45
Gly Tyr Val Ser Tyr Ser Gly Ser Thr Tyr Tyr Asn Pro Ser Leu Lys
 50                  55                  60
Ser Arg Ile Ser Ile Thr Arg Asp Thr Ser Lys Asn Gln Tyr Tyr Leu
 65                  70                  75                  80
Asp Leu Asn Ser Val Thr Thr Glu Asp Thr Ala Thr Tyr Tyr Cys Ala
                 85                  90                  95
Asn Trp Asp Gly Asp Tyr Trp Gly Gln Gly Thr Leu Val Thr Val Ser
            100                 105                 110

<210> SEQ ID NO 27
<211> LENGTH: 339
<212> TYPE: DNA
<213> ORGANISM: Mouse
<220> FEATURE:
<221> NAME/KEY: misc_feature
<222> LOCATION: (1)..(339)
<223> OTHER INFORMATION: encoding VH_HEL

<400> SEQUENCE: 27
gatatccagc tgcaggagtc gggcccgagc ctcgtcaagc cgtcgcagac cctgtcgctc        60
acctgcagcg tcaccggcga ctcgatcacc tcggactact ggtcgtggat ccgcaagttc       120
cccggcaacc gcctcgagta catgggctac gtcagctact cgggcagcac ctactacaac       180
ccctcgctga agagccgcat ctcgatcacc cgcgacacct ccaagaacca gtactacctg       240
gacctcaact cggtcaccac cgaggacacc gccacctact actgcgcgaa ctgggacggc       300
gactactggg gccagggcac cctcgtcacc gtctccgcg                              339

<210> SEQ ID NO 28
<211> LENGTH: 75
<212> TYPE: DNA
<213> ORGANISM: Artificial
<220> FEATURE:
<223> OTHER INFORMATION: SiscFv-B; primer for PCR amplification
<220> FEATURE:
<221> NAME/KEY: misc_feature
<222> LOCATION: (1)..(5)
<223> OTHER INFORMATION: n stands for any one of A, G, C and T

<400> SEQUENCE: 28
nnnnnacggc cggcggggc ggtagcggcg gtggcgggtc gggcggtggc ggatcggata         60
tccagctgca ggagt                                                         75

<210> SEQ ID NO 29
<211> LENGTH: 66
<212> TYPE: DNA
<213> ORGANISM: Artificial
<220> FEATURE:
<223> OTHER INFORMATION: SiscFV-F; primer for PCR amplification
<220> FEATURE:
<221> NAME/KEY: misc_feature
<222> LOCATION: (1)..(5)
<223> OTHER INFORMATION: n stands for any of A, G, C and T

<400> SEQUENCE: 29
nnnnncgtgg gggtgcttgt ggtgcacgtg catggggatg ctacccgcgg agacggtgac        60
gagggt                                                                   66

<210> SEQ ID NO 30
<211> LENGTH: 11
<212> TYPE: PRT
<213> ORGANISM: Artificial
```

```
<220> FEATURE:
<223> OTHER INFORMATION: SBA-15-binding peptide

<400> SEQUENCE: 30

Ile Pro Met His Val His His Lys His Pro Arg
1               5                   10

<210> SEQ ID NO 31
<211> LENGTH: 75
<212> TYPE: DNA
<213> ORGANISM: Artificial
<220> FEATURE:
<223> OTHER INFORMATION: SiscFv-B2; Primer for PCR amplification
<220> FEATURE:
<221> NAME/KEY: misc_feature
<222> LOCATION: (1)..(5)
<223> OTHER INFORMATION: n stands for any of A, G, C and T

<400> SEQUENCE: 31
nnnnnacggc cggcgggggc ggtagcggcg gtggcgggtc gggcggtggc ggatcggata      60
tccagctgca ggagt                                                      75

<210> SEQ ID NO 32
<211> LENGTH: 68
<212> TYPE: DNA
<213> ORGANISM: Artificial
<220> FEATURE:
<223> OTHER INFORMATION: SiscFv-F2; primer fore PCR amplification
<220> FEATURE:
<221> NAME/KEY: misc_feature
<222> LOCATION: (1)..(5)
<223> OTHER INFORMATION: n stands for any of A, G, C and T

<400> SEQUENCE: 32
nnnnnccgcg ggtggtgctt gtggtgcacg tgcatgggga tgctacccgc ggagacggtg      60
acgagggt                                                              68

<210> SEQ ID NO 33
<211> LENGTH: 12
<212> TYPE: PRT
<213> ORGANISM: Artificial
<220> FEATURE:
<223> OTHER INFORMATION: SBA-15-binding peptide

<400> SEQUENCE: 33

Ile Pro Met His Val His His Arg His Pro His Val
1               5                   10

<210> SEQ ID NO 34
<211> LENGTH: 68
<212> TYPE: DNA
<213> ORGANISM: Artificial
<220> FEATURE:
<223> OTHER INFORMATION: SiscFv-F3; Primer for PCR amplification
<220> FEATURE:
<221> NAME/KEY: misc_feature
<222> LOCATION: (1)..(5)
<223> OTHER INFORMATION: n stands for any of A, G, C and T

<400> SEQUENCE: 34
nnnnngacgt gggggtgcct gtggtgcacg tgcatgggga tgctacccgc ggagacggtg      60
acgagggt                                                              68

<210> SEQ ID NO 35
<211> LENGTH: 12
<212> TYPE: PRT
<213> ORGANISM: Artificial
```

```
<220> FEATURE:
<223> OTHER INFORMATION: SBA-15-binding peptide

<400> SEQUENCE: 35

Ile Pro Met Arg Val His His Lys His Pro His Val
1               5                   10

<210> SEQ ID NO 36
<211> LENGTH: 68
<212> TYPE: DNA
<213> ORGANISM: Artificial
<220> FEATURE:
<223> OTHER INFORMATION: SiscFv-F4; Primer for PCR amplification
<220> FEATURE:
<221> NAME/KEY: misc_feature
<222> LOCATION: (1)..(5)
<223> OTHER INFORMATION: n stands for any of  A, G, C and T

<400> SEQUENCE: 36
nnnnngacgt gggggtgctt gtggtgcact ctcatgggga tgctacccgc ggagacggtg      60
acgagggt                                                              68
```

ORGANIC MATERIAL-IMMOBILING STRUCTURE AND METHOD FOR PRODUCTION OF THE SAME, AND PEPTIDE AND DNA THEREFOR

TECHNICAL FIELD

The present invention relates to an organic material-immobilizing substrate that immobilizes an organic material on its surface having at least in part a silicon oxide layer, and a method for production of the same, to a peptide having an affinity for a layer containing silicon oxide, which is used for immobilization of the organic material, and to a DNA encoding the peptide. More particularly, it relates to a biomaterial-immobilizing substrate applicable to a detector, reactor, separator or collector that utilizes a biomaterial immobilized on the substrate, and a method for production of the same.

BACKGROUND ART

Research and development have been conducted on so-called biosensors and bioreactors that utilize the molecular recognition function and/or substance conversion capability of biomaterials such as nucleic acid (DNA or RNA), enzymes and antibodies, aiming at a wide range of applications thereof.

Concerning the biosensor, further technological development is required to be applied for detection of a wide variety of objects, with increasing concern about problems of environmental pollutants, social safety and health. Concerning the bioreactor, it attracts attention more and more as an environmentally friendly clean process, and further technological development is required, for example development of production methods utilizing various bioprocesses.

More specifically, concerning the biosensor, detectors utilizing specificity of molecular recognition of a biomaterial are now widely developed. For example, there have been developed biosensors such as a DNA sensor chip utilizing base sequence-dependent complementary hydrogen bonding between deoxyribonucleic acid (DNA) strands (hybridization reaction between complementary strands); an antibody sensor for detecting disease markers and the like in the blood utilizing the molecular recognition function of an antigen-antibody reaction, that is, specific binding between a protein molecule and a small molecule or between protein molecules; and an enzyme sensor that detects the concentration of a substance utilizing an enzyme such as oxidoreductase and hydrolase, represented by a glucose sensor for diabetes patients.

Currently, these biosensors are generally used in a form of the biomaterial-immobilizing substrate in which a biomaterial such as nucleic acid molecules (e.g., DNA), and proteins such as antibodies and enzymes is immobilized on the surface of a substrate or carrier.

One of the performances required for developing biosensors is "high sensitivity and miniaturization" represented by μ-TAS (micro-Total Analysis Systems). For achieving the goal of "high sensitivity and miniaturization", it is an important technical challenge how to increase the sensitivity as well as how to use the space of very small reaction or detection field effectively.

For example, in the detection field having a biomaterial immobilized on a substrate, non-specific adsorption of biomaterials in addition to the specific binding of the target substance may occur, or the target substance itself is nonspecifically adsorbed on the substrate. These nonspecific adsorption phenomena are one of the factors reducing the S/N ratio of the biosensor. Particularly, as the detection field decreases in size, the total amount of the specifically bound target substance decreases, making the influence of the noise due to nonspecific adsorption substantial, hampering highly sensitive measurement. Furthermore, in view of effective utilization of a sample in a very small amount, non-specific adsorption of the target substance makes measurement of sufficiently high accuracy difficult. Therefore, reduction and inhibition of nonspecific adsorption phenomena is an important technical challenge.

On the other hand, concerning the bioreactor, instead of direct use of microorganisms that can produce a desired product, food additives such as amino acids, pharmaceutical candidate substances and antibiotics are now produced by enzyme reactions utilizing the site-specific catalytic property of enzymes. Further, application of enzyme reaction in production of chemical products and polymer materials is now under development. In development of such bioreactors utilizing enzyme reactions, development of apparatuses suitable for small-quantity and multi-product production has become mainstream. For example, as the technique of screening of candidate substances by the combinatorial chemistry method has come into wide use, needs for downsizing of the apparatus for small quantity production are increasing, e.g., apparatuses having immobilized enzyme protein for reaction as with the case of the biosensor.

Furthermore, materials of the substrate or carrier for the biomaterial immobilization that are utilized in the biosensor and bioreactor are generally selected from known materials such as organic polymers, glass, ceramics and metal substrates depending on the type and application of the immobilized organic material or biomaterial.

When the target substance that specifically interacts with the immobilized organic material on the substrate is a biomaterial, especially a protein, and the substrate surface is hydrophobic, nonspecific adsorption of the target substance onto such a hydrophobic surface will increase. Thus, sufficient detection sensitivity cannot be achieved with the biosensor, and high productivity may not be achieved with the bioreactor.

One of methods for reducing nonspecific adsorption onto the hydrophobic surface is to render the substrate surface hydrophilic, at least part of the substrate surface such as channels and reaction fields that contact a liquid containing the target substance. From the substrate surface subjected to the hydrophilicity treatment, the target substance protein physically adsorbed on the surface can be removed relatively easily by washing with a cleaning aqueous solution of a desired composition. Popular methods for rendering the substrate surface hydrophilic include a method of providing on the surface a metal oxide layer represented by silicon oxide, and a method of forming a hydrophilic coat of a coupling agent represented by a silane coupling agent.

To immobilize biomaterials such as proteins on the surface of a substrate subjected to the hydrophilic treatment, there is, for example, immobilization of a protein on the substrate surface by physical adsorption by immersing the substrate in a protein solution or coating the substrate with a protein solution to form a coating layer of the protein solution on the substrate surface, and then removing/drying the solvent contained in the coating layer, or a method of chemical immobilization by chemically modifying the substrate surface or protein molecules for the purpose of introducing reactive functional groups, and then forming a chemical bond through a reaction between introduced reactive functional groups.

As one example of the physical adsorption immobilization method, Japanese Published Patent Application No. H06-

003317 discloses a method for preparation of an enzyme electrode applying a method of forming an organic charge transfer complex layer on the surface of a conductive substrate, and then coating the organic charge transfer layer with a protein solution and then drying the layer to physically adsorb and immobilize an enzyme protein on the substrate surface via the organic charge transfer layer.

As one of the chemical immobilization method, Sensor and Actuators B 15-16 p 127 (1993) discloses a method of treating the platinum-deposited surface of a silicon substrate with an amine based silane coupling agent, and then using a cross-linking agent such as glutaraldehyde to link an amino group of the amino silane coupling with a peptide chain via chemical bonding. Another example is, in preparation of a detector such as a biosensor having an immobilized antibody on a glass substrate, a method that introduces reactive functional groups to the surface of a glass substrate by the silane coupling agent treatment, and similarly uses a cross-linking agent to immobilize peptide chains through chemical bonds.

However, in the method of utilizing chemical binding by the physical adsorption and cross-linking reaction to immobilize biomaterials, sites involved in adsorption on the protein side can not be freely selected in physical adsorption onto the substrate particularly when applying to proteins such as enzymes and antibodies. Furthermore, sites in which functional groups involved in the reaction exist on the protein side for the cross-linking agent cannot be freely set, and when a plurality of functional groups capable of reaction exist, selectivity among the groups is extremely low. That is, in binding to the substrate through chemical bonds by the physical adsorption and cross-linking reaction, sites involved in binding on the protein side are randomly selected, and therefore if the sites directly involved in or indirectly related to the capability of the protein binding to an object compound, the enzyme activity of the protein and the like are also involved in binding to the substrate surface, the capability of binding to the object and the enzyme activity, which are possessed by the protein, may be significantly reduced when the sites bond to the substrate.

Thus, development of means for previously setting immobilized sites on the non-immobilized molecule side, which are involved in binding to the substrate surface, for example a technique capable of previously controlling the orientation of biomaterials immobilized on the substrate surface becomes important.

In addition, in achievement of "high sensitivity and miniaturization", it is necessary to highly integrate and immobilize biomaterials in very small areas on the substrate surface.

As one example of the method for highly integrating and immobilizing biomaterials, a method of employing as a substrate a substrate having a large specific surface area, for example a porous material having a regular nano-level microporous structure, and immobilizing biomaterials on the surface having the microporous structure having a large specific surface area is generally known. For the method of forming a regular microporous structure on the scale of nanometer order capable of being used for the above-described application, polymer-processed membrane filters, porous glass, anode-oxidized aluminum films, and the like are well known. Furthermore, a method of forming a porous coated film on the surface of a substrate such as a metal or glass by a coating process is also known. In the method described in Science 279 548 (1997), as a method for forming the porous film, a structure having silica formed around a nonionic block polymer as a mold under acidic conditions using alkoxy silane as a starting material is first formed. Then, the nonionic block polymer as a mold is eliminated by heating or treatment with an organic solvent, whereby a silica film of porous structure having a pore diameter in the order of several nanometers. By using as a substrate such a porous material having a pore diameter in the order of several nanometers, a reaction field having immobilized thereon biomaterials in an amount sufficient for high sensitive detection can be prepared even in a very small area.

Examples of the method utilizing the porous substrate, especially the method of immobilizing biomaterials such as proteins to a porous silicon oxide material may include methods described in the following documents.

Japanese Patent Application Laid-Open No. 2000-139459 discloses extremely stable enzymes such as peroxidase, subtilisin and lipase immobilized in micropores of a mesoporous silica porous material having an anionic surface by means of the van der Waals force.

Japanese Patent Application Laid-Open No. 2001-128672 also discloses a method of degrading a lignin substrate by peroxidase immobilized in micropores of a mesoporous silica porous material.

Further, also using a method of immobilizing an enzyme protein on a porous substrate, Japanese Patent Application Laid-Open No. 2001-46100 discloses a method for enzymically modifying a fuel, Japanese Patent Application Laid-Open No. 2001-178457 discloses a method for immobilizing an enzyme, and Japanese Patent Application Laid-Open No. 2002-95471 discloses a method for improving the substrate specificity of lipase, a lipid-degrading enzyme.

Further, it is reported that immobilization of enzyme proteins such as cytochrome c, papain and trypsin in a mesoporous molecular sieve of silicon oxide improves the performance of these enzymes (Journal of Molecular Catalysis. B, 2(2-3), 115-126 (1996)).

It is also reported that immobilization of an enzyme protein (α-chymotrypsin) in micropores of nanoporpus sol-gel glass by covalent binding utilizing a silanizing agent (trimethoxyl propanal) having an aldehyde group at the terminus can improve the stability of the enzyme protein (Biotechnology and Bioengineering, 74 (3), 249-255 (2000)).

DISCLOSURE OF THE INVENTION

By employing the above substrate having a large specific surface area, for example, a porous material having a nano level regular microporous structure as a substrate, a larger amount of a biomaterial can be immobilized on the substrate surface, but if the biomaterial immobilized on the substrate is not in a conformation suitable for binding the target substance to be detected, for example, detection sensitivity matching the amount of the immobilized biomaterials cannot be obtained. Also, unless the biomaterial is in an appropriate conformation with respect to the target material with which it reacts, reactivity matching the amount of the immobilized biomaterial cannot be obtained. That is, unless the biomaterial is immobilized on the substrate with a conformation suitable for its application, the advantage associated with immobilization of a larger amount of a biomaterial on the substrate surface using a substrate having a large specific surface area cannot be exhibited.

In other words, unless the biomaterial molecules are immobilized on the substrate under control of orientation suitable for its application, the amount of biomaterial immobilized on the substrate should be further increased for obtaining desired detection sensitivity or reactivity, and therefore an excessive amount of biomaterials must be immobilized per unit area of the substrate, or the area of the substrate on which the biomaterials are immobilized must be excessively increased. Excessively increasing the area of the substrate on which the biomaterial molecules are immobilized causes a significant problem in achieving downsizing of the apparatus. On the other hand, if the amount of a biomaterial costly in fabrication is increased, the total cost for the apparatus increases, thus causing a significant problem in reduction of the necessary process cost.

Thus, it is desired to develop an immobilization method with orientation control that enables the biomaterial immobilized on a substrate to have conformation suitable for its application, utilizing a substrate having a large specific surface area to immobilize a larger amount of a biomaterial on the surface of the substrate.

The present invention solves the aforementioned problems when an organic material, especially a biomaterial, is immobilized on the substrate to be used as a biosensor or bioreactor, and its object is to provide an organic material-immobilizing structure employing new immobilization means that can stably immobilize an organic material, especially a biomaterial on the surface of a substrate in an orientation suitable for exhibition of the physiological functions thereof, as well as a preparation method utilizing the new immobilization means. In addition, the present invention provides a peptide having an affinity for a layer containing silicon oxide usable as new immobilization means, and DNA coding for the peptide.

For solving the problems described above, the inventors studied new immobilization means usable in immobilization of an organic material, especially a biomaterial, to the surface of a substrate, and found out that if a member serving for immobilization is provided separately from the main body of the organic material and this member binds to the surface of the immobilization site through a specific physical interaction between the member and the surface, not by using a chemical reagent, the organic material can sufficiently exhibit their original physiological functions, the organic material can be stably immobilized on the surface of the immobilization site with a conformation suitable for exhibition of the physiological functions of the organic material, especially biomaterials. Further, the inventors found out that when a silicon oxide containing member is utilized as the surface of the immobilization site, a peptide having an affinity for silicon oxide can be selected, and a binding domain including the peptide having an affinity for silicon oxide fused to a functional domain containing the organic material, especially a biomaterial, can immobilize the organic material with high reproducibility and stability to a substrate having a silicon oxide surface through physical binding between the surface silicon oxide and the binding domain including the peptide having an affinity for silicon oxide, in an orientation suitable for exhibition of physiological functions possessed by the organic material especially a biomaterial. The present invention has been completed based on these findings.

The present invention relates to a structure having an organic material immobilized on the surface of a substrate, characterized in that at least a part of the surface of said substrate comprises one or more members containing silicon oxide, said organic material is bound to the surface of said substrate through a binding domain containing at least a peptide capable of binding to silicon oxide, and said peptide comprises at least one amino acid sequence selected from the group consisting of the following amino acid sequences: SEQ ID NO: 1; Val-Ser-Pro-Met-Arg-Ser-Ala-Thr-Thr-His-Thr-Val; and SEQ ID NO: 2; Ile-Pro-Met-His-Val-His-His-Lys-His-Pro-His-Val; or an amino acid sequence with one or several amino acids deleted from, substituted in or added to the selected amino acid sequence, or a repeating structure or combination thereof.

Furthermore, the present invention relates to a method for production of a structure having organic material immobilized on the surface of a substrate comprising the steps of: obtaining a fusion of an organic material and a binding domain by linking an organic material to a binding domain containing at least a peptide capable of binding to silicon oxide; and binding at least a part of said binding domain to a substrate of which surface comprises at least one member containing silicon oxide, thereby immobilizing said organic material on the surface of said substrate through said binding domain, wherein said peptide comprises: at least one amino acid sequence selected from the group consisting of the following amino acid sequences: SEQ ID NO: 1; Val-Ser-Pro-Met-Arg-Ser-Ala-Thr-Thr-His-Thr-Val; and SEQ ID NO: 2; Ile-Pro-Met-His-Val-His-His-Lys-His-Pro-His-Val; or an amino acid sequence with one or several amino acids deleted from, substituted in or added to the selected amino acid sequence, or a repeating structure or combination thereof.

Furthermore, the present invention relates to a peptide having an affinity for silicon oxide comprising: at least one amino acid sequence selected from the group consisting of the following amino acid sequences: SEQ ID NO: 1; Val-Ser-Pro-Met-Arg-Ser-Ala-Thr-Thr-His-Thr-Val; and SEQ ID NO: 2; Ile-Pro-Met-His-Val-His-His-Lys-His-Pro-His-Val; or an amino acid sequence with one or several amino acids deleted from, substituted in or added to the selected amino acid sequence, or a repeating structure or combination thereof.

Furthermore, the present invention relates to a DNA encoding a peptide having an affinity for silicon oxide, said peptide comprises: at least one amino acid sequence selected from the group consisting of the following amino acid sequences: SEQ ID NO: 1; Val-Ser-Pro-Met-Arg-Ser-Ala-Thr-Thr-His-Thr-Val; and SEQ ID NO: 2; Ile-Pro-Met-His-Val-His-His-Lys-His-Pro-His-Val; or an amino acid sequence with one or several amino acids deleted from, substituted in or added to the selected amino acid sequence, or a repeating structure or combination thereof.

Furthermore, the present invention relates to a vector including a DNA encoding a peptide having an affinity for silicon oxide, wherein said peptide comprises: at least one amino acid sequence selected from the group consisting of the following amino acid sequences: SEQ ID NO: 1; Val-Ser-Pro-Met-Arg-Ser-Ala-Thr-Thr-His-Thr-Val; and SEQ ID NO: 2; Ile-Pro-Met-His-Val-His-His-Lys-His-Pro-His-Val; or an amino acid sequence with one or several amino acids deleted from, substituted in or added to the selected amino acid sequence, or a repeating structure or combination thereof.

Furthermore, the present invention relates to a detector for detecting a target substance in a sample comprising: means for contacting a structure according to claim 1 with a sample whereby said organic material is bound to said target material in the sample; and means for detecting said bound target material.

Furthermore, the present invention relates to a detection method for detecting a target substance in a sample, specimen comprising the steps of: contacting a structure having organic material immobilized on the surface of the substrate according to claim 1 with the sample to bind said organic material to said target substance of the specimen; and means for detecting said bound target substance.

In the organic material-immobilizing structure according to the present invention, for example, in a substrate having an immobilized biomaterial on the surface, a silicon oxide layer is provided as the substrate surface to immobilize the biomaterial thereon, and the organic material is immobilized through a binding domain that can bind to the silicon oxide layer and linked to the functional domain being the biomaterial itself, whereby the biomaterial portion can be selectively immobilized to the substrate without directly contacting the substrate surface. By immobilizing a biomaterial on the substrate surface through a separate binding domain, immobilization itself does not affect the original function of the biomaterial, and the function is not affected since no chemical reaction is required for immobilization.

In addition, in the biomaterial-immobilizing substrate of the present invention, the biomaterial to be immobilized (functional domain) is first fused to a binding domain capable of binding to a silicon oxide layer, and then immobilized to the substrate via the binding domain. Thus various peptides having a binding capability to the silicon oxide layer can be selected as the binding domain, irrespective of the type and function of the biomaterial serving as the functional domain. In other words, in the organic material-immobilizing structure according to the present invention, the organic material, especially a biomaterial, can be immobilized by appropriately selecting the amino acid sequence of a peptide in the binding domain, maintaining the original function level. Thus, a wide variety of organic materials can be immobilized.

BEST MODE FOR CARRYING OUT THE INVENTION

In an organic material-immobilizing structure according to the present invention, an organic material is specifically immobilized on the surface of a substrate having one or more members containing silicon oxide on at least part of the surface, through a binding domain fused to the organic material, not through conventional physical adsorption or covalent bonding to the silicon oxide layer. Such a binding domain can be designed based on the amino acid sequences screened from a random peptide library for binding ability to silicon oxide.

Thus, when the organic material-binding domain fusion is a fusion of a biomaterial and a binding domain, it can be previously confirmed that the fusion maintains the original function (molecular recognition function and catalytic property) of the biomaterial. Then the fusion can be immobilized on the surface of the silicon oxide containing member without chemical reaction using a reagent etc. that may affect the function of the biomaterial. Therefore the biomaterial immobilized on the surface of the silicon oxide-containing member can exhibit its function sufficiently. In addition, since an amino acid sequence having a desired binding ability to the silicon oxide member on the substrate surface can be selected by screening before hand. Furthermore, both the linkage form of the binding domain to the biomaterial and the amino acid sequence required for binding to the silicon oxide can be designed. Therefore, the organic material-immobilizing structure according to the present invention may have a wide application range to both silicon oxide and the organic material, especially biomaterial.

The present invention is described more in detail below.

In the organic material-immobilizing structure according to the present invention, an area comprised of one or more members containing silicon oxide is provided on at least a part of the surface of a substrate to which an organic material is. Immobilization to the silicon oxide area is done by the binding of at least a part of the binding domain containing a peptide of at least one amino acid. Thus, owing to the selective binding of the binding domain to the area comprised of the members containing silicon oxide, the physical adsorption of the organic material bonded to the binding domain to the substrate is prevented, so that the function of the organic material would not be affected by physical adsorption.

Figure 1:
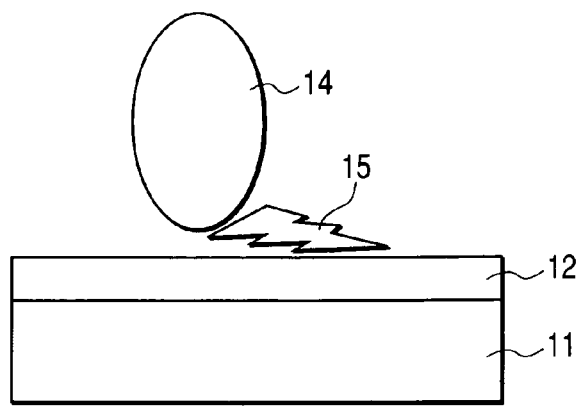
FIG. 1 is a sectional view schematically showing the configuration of a structure in one example of an organic material-immobilizing structure according to the present invention shown in Example 5.

FIG. 1 schematically shows one embodiment of the organic material-immobilizing structure according to the present invention. In the embodiment shown in FIG. 1, the base material is a flat substrate 11, and the surface thereof is provided with a silicon oxide layer 12 as a coating layer comprising members containing silicon oxide. The organic material is selectively immobilized on the surface of the silicon oxide layer 12 through a binding domain 15. The organic material itself, corresponding to a functional domain 14 linked to the binding domain 15, may cause nonselective weak physical adsorption to the silicon oxide layer 12, but the binding domain 15 will bind to the silicon oxide layer 12 more selectively. Thus, the frequency of physical adsorption of the organic material is low owing to such a competitive process, and nonspecific weak physical adsorption can be reduced by selecting immobilization conditions.

Thus, any appropriate substrate can be used so long as a coated layer made of a member containing silicon oxide can be provided on its surface. Specifically, it may be a substrate formed from: a metal material such as iron, aluminum and gold; a synthetic resin material represented by polystyrene, PMMA and PC, a semiconductor material such as silicon, oxides; and ceramic materials such as alumina and sapphire, or composite materials of two or more of these material.

On the other hand, for the coating layer comprised of a member or members containing silicon oxide, which is provided on the surface of the substrate, silicon oxide is exposed on the outermost surface. The silicon oxide layer 12 can be prepared by, for example, coating the substrate surface with a solution containing a raw material such as alkoxy silane, a polymerization initiator, a metal catalyst and the like as necessary by a known method to form a silicon oxide by polymerization through the processes of solvent evaporation, drying and heating.

Alternatively, the silicon oxide layer 12 provided on the substrate surface can be formed by the CVD method. When the CVD method is applied, heating at considerably high temperature is done in the deposition process, and therefore the base material should be a material insusceptible to heat damages due to the heating at a high temperature. In addition, if there is a large difference between the coefficient of thermal expansion of the deposited silicon oxide layer and that of the substrate, mechanical deformation may occur in the silicon oxide layer during cooling after the deposition, resulting in flaking or warping. Therefore the substrate material is preferably selected in consideration of this aspect.

For setting the thickness of the silicon oxide layer 12 to a nanometer order, it is preferable to use a vapor phase deposition method such as the DVD method more suitable for formation of a very thin silicon oxide film.

In general, porous silicon oxide layer 12 is preferable, because it has a larger specific surface area due to micropores, thus making it possible to increase a total surface area usable for immobilization. In the present invention, when organic material is immobilized in micropores of the porous material, the inner diameter of the micropore is preferably optimized according to the shape of the organic material to be immobilized, so that immobilization through selective binding by the binding domain is performed rather than physical adsorption of the organic material itself. Furthermore, when the silicon oxide layer 12 is formed into a porous coating structure, the thickness of the silicon oxide layer 12 is also preferably optimized according to the above-described inner diameter of the micropores as well as the shape of the organic material to be immobilized.

For forming the silicon oxide layer having a porous coating structure, for example, a coating layer is formed with an alkoxy silane solution containing a surfactant under acidic conditions, which is reacted at 35° C. for 20 hours, and then dried at 80° C. for 48 hours to form a silicon oxide layer in which the surfactant phase is coexisting in a network form. In this case, vapor phase deposition method such as CVD method is not preferable. Then, the surfactant phase coexisting in the layer is removed (e.g. by heating at 500° C. for 6 hours), whereby regions occupied by the surfactant are left as a microporous structure having a pore size of 1 to 1000 nm. Another method for removing the surfactant from the silicon oxide-surfactant complex prepared by the above process is treating with an organic solvent to extract the surfactant. For which method should be employed, it is preferable that any of these methods is appropriately selected and used according to the properties of the substrate, e.g. heat resistance, solvent resistance, etc.

As already described above, when the silicon oxide layer is formed to have a porous coating structure, there is an advantage that the specific surface area can be considerably increased, thus making it possible to increase the number of biomaterials immobilized per unit area. Furthermore, there is also an advantage that the micropores in which the biomaterial is immobilized has a further function of selecting molecules entering the molecule recognition reaction field according to the size of the micropore. Further, the volume of each reaction field in the micropore is limited and small in comparison with biomaterial immobilized on a flat surface. Accordingly, it can be expected that in the reaction field in the micropore having a limited space, a required average travel length can be significantly reduced when the target compound binds to the biomaterial, thus exhibiting an effect of improvement in molecule recognition reaction efficiency. Thus, the micropore size can be selected within a range allowing the desired target compound to selectively enter the micropore in consideration of the size of the target compound and the viscosity of the sample solution. For example, the micropore size is selected within the range of 1 to 500 nm, preferably 10 to 300 nm.

As described above, the silicon oxide layer can be prepared using a method of vapor deposition onto the substrate surface directly from a vapor phase, or a method of processing a coating film to form the layer. Furthermore, when an organic material is employed for the substrate, the temperature selected in a step of forming the silicon oxide, a solvent capable of being used, and the like are appropriately selected according to the type of substrate material. In some cases, silicon oxide material particles are previously formed, and suspended in a solvent selected in view of the nature of the substrate material, and the suspension of silicon oxide material particles is applied, and the solvent is removed by heating as required, whereby a layer containing granular silicon oxide can be formed.

Moreover, by preparing the substrate itself with a light transmitting material, a structure may be provided such that the behavior of the biomaterial immobilized on the surface thereof can be determined by an optical method.

In the present invention, the organic material to be immobilized on the substrate surface is appropriately selected according to the purpose of usage of the organic material-immobilizing structure prepared. The type of organic material utilized as the functional domain is not specifically limited as long as it can be at least linked to the binding domain containing a peptide of one or more amino acids. Various biomaterials capable of being linked to the binding domain containing a peptide of one or more amino acids can be selected as the organic material to be immobilized on the substrate surface. Specifically, examples of biomaterials selectable as organic material to which the present invention can be applied may include nucleic acid molecules, amino acids, peptides or proteins, polysaccharides and polysaccharide-protein complexes.

For instance, examples of nucleic acid molecules may include deoxyribonucleic acid molecules and ribonucleic acid molecules. For example, in a DNA chip or the like, a mechanism recognizing a nucleic acid molecule having a base sequence complementary to a base sequence of a DNA molecule immobilized through a hybridization reaction is utilized, and therefore the DNA molecule is a single-stranded DNA molecule having a predetermined base sequence. In addition, it is also known that some of nucleic acid molecules form a specific tertiary structure, and have a molecular recognition function derived from such a tertiary structure. The nucleic acid molecules having such a molecular recognition function are collectively called aptamer and. for example, base sequences having a high molecular recognition function can be selectively obtained from various base sequences by a molecular evolution engineering represented by the SELEX method. Further, target dsDNA sequences of DNA binding proteins have been identified, these types of double-stranded DNA molecules can be selected as the organic material to which the present invention is applicable.

Furthermore, examples of protein molecules capable of selecting organic material to which the present invention is applicable include enzyme, antibody, receptor molecules or scaffold proteins.

Antibody molecules to which the present invention is applicable include natural antibody molecules produced as a result of an immune reaction against an antigen material introduced into a subject animal, and recombinant antibody molecules having a structure modified partially or wholly by genetic engineering. These antibodies may be monoclonal antibodies or polyclonal antibodies. These antibody molecules may be of any immune globulin class, and can be selected from, for example, human IgG, IgM, IgA, IgD and IgE. Among these classes, antibody molecules of the IgG can be used more suitably.

In addition to the above immune globulin molecules, antibody fragments may be used, including Fab, Fab' and F(ab')$_2$. For example, Fab fragments are those similar to the antibody fragments by papain digestion. F(ab')$_2$ fragments are those similar to the pepsin-digested antibody fragments. These antibody fragments may be prepared by cleaving antibody enzymatically or chemically, but in many cases, by recombination production in genetic engineering. Further, scFv (single chain Fv) may be used, which is a recombinant molecule having an antigen recognition function, produced linking heavy chain portion (VH) and a light chain portion (VL) with a peptide linker to reconstitute a variable domain (Fv) being the antigen recognition site in the immune globulin molecule.

For example, if the biomaterial as the functional domain 14 is a protein feasible for recombination-production, the functional domain and the binding domain containing a binding peptide can be made into a fusion protein in which both peptide chains are linked in tandem. In this case, a linker sequence of appropriate amino acid length can also be inserted between the functional domain 14 and the binding domain 15.

On the other hand, if the biomaterial, to which the present invention is applied, is a protein of unknown sequence, nucleic acid or polysaccharide, this biomaterial, or the binding domain containing a peptide structure, or both, are subjected to chemical modification/conversion such as introduction of reactive functional groups used for linkage between them with in a range not significantly influencing their functions, after which a complex with the biomaterial and the binding domain linked by chemical binding can be prepared. Specifically, the biomaterial, the binding domain, or both are previously subjected to chemical modification/conversion to provide one of the following combinations: maleimide group and sulfhydryl group (—SH), succimide group and amino group, isocyanate group and amino group, halogen and hydroxy group, halogen and sulfhydryl group (—SH), epoxy group and amino group, and epoxy group and sulfhydryl group (—SH), and thereafter a chemical bond can be formed between the above-described functional groups, whereby a fusion of the biomaterial and the binding domain can be formed.

Further, if the biomaterial, to which the present invention is applied, is a lipid, it is possible to prepare a binding domain that has a hydrophobic peptide structure comprised of amino acids having free hydrophobic groups such as alanine, valine, leucine, isoleucine, methionine, tryptophane, phenyl alanine and proline, in addition to the silicon oxide-binding peptide structure. A complex of the lipid and the binding domain is prepared by hydrophobic binding of the lipid to the hydrophobic peptide structure of the binding domain.

In the organic material-immobilizing structure according to the present invention, the binding domain 15, which serves for in immobilization to the surface of the silicon oxide layer provided on the substrate surface, contains a peptide of one or more amino acids having a specific binding ability to the silicon oxide layer 12, or it is a protein containing the amino acid sequence of such a peptide.

A preferred example of the amino sequence having an affinity for the silicon oxide layer, contained by the binding domain, is at least one sequence selected from the group consisting of: Val-Ser-Pro-Met-Arg-Ser-Ala-Thr-Thr-His-Thr-Val SEQ ID NO: 1; and Ile-Pro-Met-His-Val-His-His-Lys-His-Pro-His-Val SEQ ID NO: 2, but may be a partial peptide of SEQ ID NO: 1, or SEQ ID NO: 2.

Furthermore, it may have a repeating structure of all or part of the above-described amino acid sequence.

Furthermore, it may be a combination of these sequences.

Further, the amino sequence of one or more amino acids having an affinity for the silicon oxide layer, which is possessed by the above-described binding domain, may be an amino acid sequence determined by screening of a random peptide library on the affinity for the silicon oxide layer, or an amino acid sequence rationally designed according to the chemical nature of the silicon oxide layer.

A method for screening of the random peptide library for obtaining an amino acid sequence having an affinity for the silicon oxide layer is described below.

Random peptide libraries capable of being used for screening may include a random synthetic peptide library of random peptides chemically synthesized in a soluble form, a solid phase peptide library synthesized on resin beads, and an in vitro synthesized peptide library synthesized using chemically synthesized random DNAs and a cell-free ribosome system, a phage display peptide library prepared by linking a random synthetic gene to a gene of a surface protein of M13 phage (e.g. gene III protein) at its N-terminus, and libraries of random peptides displayed as a fusion to a bacterial outer membrane protein Omp A (Francisco et al., 1993, Proc. Natl. Acad. Sci. USA, 90, 10444-10448 or Pistor and Hoborn, 1989, Klin. Wochenschr., 66, 110-116), PAL (Fuchs et al., 1991, Bio/Technology, 9, 1369-1372), or Lamb (Charbit et al., 1988, Gene, 70, 181-189 and Bradbury et al., 1993, Bio/Technology, 1565-1568), fimbrin (Hedeg Aard and Klem M., 1989, Gene, 85, 115-124 and Hofnung, 1991, Methods Cell Biol., 34, 77-105), and IgA protease β region (Klauser et al., 1990, EMBO J., 9, 1991-1999).

The following methods can be used for screening amino acid sequences having an affinity for the silicon oxide layer using these random peptide libraries. With a synthetic peptide library, the peptide library is brought into contact with a carrier of the same material as the silicon oxide layer 2 in the form of column, plate or substrate to cause adsorption, then peptides having no affinity for the carrier are removed through a cleaning step, peptides bound to the silicon oxide carrier are thereafter collected, and their amino acid sequences are determined using Edman degradation or the like.

When the phage display library is used, the library is brought into contact with the above carrier or the silicon oxide coating substrate, and the non-specifically bound phages are washed away. Phages remaining after washing are eluted with an acid or the like, neutralized with a buffer, and then used to infect E. coli to amplify phages. When this selection (panning) is repeated two or more times, a plurality of clones having a desired affinity for the silicon oxide layer are concentrated. Here, for obtaining a single clone, E. coli cells infected with phages are spread on a agar plate to form colonies, and each single colony is cultured in a liquid culture, then phages existing in supernatant liquid of the culture medium are precipitated and purified with polyethylene glycol or the like, and the base sequences thereof are analyzed, whereby the amino acid sequence of the desired peptide can be known.

Screening of peptides having an affinity for the silicon oxide layer using the phage display peptide library includes a step of concentrating phages more strongly bonded to silicon oxide, so called a panning operation, and is thus capable of selecting more reliable peptide candidates, and therefore can be suitably used for the object of the present invention. As a method for constructing the phage display random peptide library, for example, each random synthetic gene is linked to a gene of a surface protein of M13 phage (e.g. gene III protein) at its N-terminus to form a library. Methods thereof are reported in Scott, J. K. and Smith, G. P., Science Vol. 249, 386 (1990), Cwirla, S. E. et al., Proc. Natl. Acad. Sci. USA Vol. 87, 6378, (1990) and the like. The size of a gene inserted is not specifically limited as long as a peptide can be stably expressed, but in order that the prepared library covers all random sequences and have an affinity, a length corresponding to 6 to 40 amino acids (equivalent to about 600 to 4000 molecular weights) is appropriate, and a length equivalent to 7 to 18 amino acids is particularly preferable.

Amino acid sequences having an affinity for the silicon oxide layer, obtained by screening of the phage display peptide library may be linked in series to constitute a repeating structure. Furthermore, if two or more types of amino acid sequences are obtained, a sequence obtained by linking all or part of appropriate amino acid sequences in tandem may be used as an amino acid sequence having an affinity for the silicon oxide layer. In this case, an appropriate spacer sequence is preferably provided between two types of amino acid sequences. The spacer sequence preferably has about 3 to about 400 amino acids, and the spacer sequence may contain any amino acids. Most preferably, the spacer sequence does not hinder the function of the above-described functional domain, and also does not hinder the binding of the biomaterial to the silicon oxide layer through the binding domain.

The amino acid sequence having an affinity for the silicon oxide layer, for use in the present invention, may be not only an amino acid sequence determined by screening of the random peptide library, but also an amino acid sequence rationally designed according to the chemical nature of the silicon oxide layer. A library is constructed with those amino acid sequences, whereby an amino acid sequence having a higher affinity can be selected by the screening method described above.

Since the silicon oxide layer 2 having a hydrophilic surface, when a sequence rich in amino acids having hydrophilic groups, particularly cationic residues and hydroxyl groups, is selected as the affinity site 15a that is fused to the functional domain 14 and translated, immobilization to the silicon oxide layer 2 through the above-described binding domain 15 can be further strengthened.

A fusion protein made by linking together a binding domain containing an amino acid sequence having an affinity for the silicon oxide layer and a protein as a functional domain having desired properties can be stably prepared by constructing an expression vector having a gene encoding a binding peptide in the upstream or downstream of a gene encoding the above-described functional domain in the same reading frame. A promoter sequence for use in the expression vector, an antibiotic-resistant gene sequence and the like may be selected from known sequences and used.

Immobilization of the fusion protein to the silicon oxide layer is attained through an amino acid sequence having an affinity for the silicon oxide layer (hereinafter referred to as silicon oxide affinity site 15a) obtained by the above-described screening operation in the above-described binding domain 15 fused to the above-described functional domain 14.

The above-described silicon oxide affinity site 15a obtained by the above method is fused to a protein as the above-described functional domain 14 by an ordinary gene engineering method. The above-described silicon oxide affinity site 15a can be linked to the N-terminus or C-terminus of the protein as the above-described functional domain 14 to be expressed. Furthermore, it can also be expressed as a binding domain with an appropriate linker sequence inserted therein.

The linker sequence preferably has about 3 to about 400 amino acids, and the linker sequence may contain any amino acids. Most preferably, the linker sequence does not hinder exhibition of functions of the protein as the above-described functional domain 14, and does not hinder the binding of the above-described binding domain 15 to the silicon oxide layer 12.

In the organic material-immobilizing structure according to the present invention, when two or more types of amino acid sequences having an affinity for the silicon oxide layer are obtained by, e.g., screening of the above-described phage display peptide library, two or more types of fusion proteins can be prepared each having a binding domain containing a different affinity amino acid sequence, and immobilized on the same substrate surface as a mixture.

As a method for separation/purification of the fusion protein containing the above-described functional domain 14 and the binding domain having the silicon oxide affinity site 15a, any method may be used as long as it can maintain the function of the functional domain.

A step of immobilizing organic material on the silicon oxide layer 12 through the binding domain containing the silicon oxide affinity site 15a is achieved by bringing a fusion of the organic material and the binding domain into contact with the silicon oxide layer 12 in an aqueous medium.

In the present invention, the composition of the aqueous medium for use in the step of performing immobilization through the binding domain may be any composition as long as it does not hinder the function of the organic material to be immobilized, such as binding reaction or material conversion reaction of a biomaterial, but may be a composition in which the binding or conversion reaction activity of the biomaterial can be expressed, to simplify subsequent steps. Here, as the composition such that the activity can be exhibited, for example, a buffer solution may be used. As the buffer solution, a general buffer solution for use in a biochemical reaction, e.g. an acetate buffer, phosphate buffer, potassium phosphate buffer, 3-(N-morpholino) propane sulfonate (MOPS) buffer, N-tris (hydroxymethyl) methyl-3-aminopropane sulfonate (TAPS) buffer, tris-chloride buffer, glycine buffer or 2-(cyclohexylamino) ethane sulfonate (CHES) buffer is suitably used. For example, if the biomaterial is a PHA synthetase protein described later, the concentration of the buffer solution such that the enzyme activity of the protein can be exhibited may be in a general range of concentrations, i.e. in the range of 5 mM to 10 M, but is preferably 10 to 200 mM. Furthermore, the pH is adjusted to be 5.5 to 9.0, preferably 7.0 to 8.5.

Immobilization of the fusion comprising the organic material and the binding domain to the silicon oxide layer 12 of the substrate surface through the binding domain 15 is achieved by preparing the liquid in which the substrate provided with the silicon oxide layer 12 is immersed as a solution having the fusion comprising the organic material and the binding domain dissolved in the above aqueous medium so that it has a predetermined concentration. At this time, it is desirable that a reaction vessel should be shaken or stirred with appropriate strength so that a binding domain portion in the fusion protein can uniformly bind to the surface of the silicon oxide layer.

The amount of surface charge and hydrophobicity of the silicon oxide layer and the silicon oxide affinity site 15a contained in the binding domain vary with the pH and salt concentration of the aqueous medium, and therefore it is desirable that in consideration thereof, the composition of the aqueous medium for use in the above immobilization processing should be determined. For example, by increasing the salt concentration, the hydrophobicity of the silicon oxide layer and the silicon oxide affinity site 15a can be enhanced.

Furthermore, a wetting angle of the solvent or the like for the silicon oxide layer 12 provided on the substrate surface is previously measured, and the hydrophilicity and hydrophobicity of the silicon oxide layer 12 are examined, whereby a solution composition suitable for binding of the binding domain can be set. Further, the amount of silicon oxide affinity site 15a bound to the surface of the silicon oxide layer 2 can be directly measured to determine the composition. The bound amount can be determined, for example, by substaction method in which a solution of a fusion at a a known concentration is added to the silicon oxide layer having a certain area to carry out immobilization, and the concentration of the fusion remaining in the solution is then measured, and the binding amount is determined by subtraction.

The organic material-immobilizing structure, e.g. a biomaterial immobilizing substrate, prepared by the above method may be directly used. Further, it may be used after being freeze-dried. Time taken for immobilization processing of biomaterials is desirably 1 minute to 48 hours, more desirably 10 minutes to 3 hours. Leaving the structure standing for an excessive amount of time may cause reduction in the desired function of immobilized biomaterials, and thus is not preferable.

Target substances of the present invention are broadly classified into non-biomaterials and biomaterials. Important non-biomaterial targets important in industrial viewpoint include PCBs of different numbers/positions of chlorine substitutes as environmental contaminants, dioxins of different numbers/positions of chlorine substitutes, and endocrine disrupting chemicals so called environmental hormones (e.g. hexachlorobenzene, pentachlorophenol, 2,4,5-trichloroacetic acid, 2,4-dichloropfenoxyacetic acid, amitrole, atrazine, arachrole, hexachlorocyclohexane, ethylparathion, chlordane, oxychlordane, nonachlor, 1,2-dibromo-3-chloropropane, DDT, kerosene, aldrin, endrin, dieldrin, endosulfan (benzoepiso), heptachlor, heptachlor epoxide, malathion, mesomil, methoxychlor, malex, nitrophene, toxaphene, trifluralin, alkyl phenol (having 5 to 9 carbon atoms), nonyl phenol, octynonyl phenol, 4-octyl phenol, bis-phenol A, di-2-ethylhexyl phthalate, butylbenzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitrotoluene, octachlorostyrene, aldicurve, venomil, kiepon (chlordecon), manzeb (mankozeb), manneb, methylam, metrivudine, sipermetrine, esphene valerate, phene valerate, permetrine, vincrozoline; zineb, ziram, dipentyl phthalate, dihexyl phthalate and dipropyl phthalate).

Target biomaterials include those selected from nucleic acids, proteins, polysaccharides, lipids and complexes thereof, more particularly those containing biomaterial molecules selected from nucleic acids, proteins, polysaccharides and lipids and specifically, the present invention may be applied to any material as long as it includes any material selected from DNAs, RNAs, aptamers, genes, chromosomes, cell walls, viruses, antigens, antibodies, lectins, haptens, hormones, receptors, enzymes, peptides, glycosphingo and sphingolipid. Further, bacteria and cells themselves producing the above-described biomaterials may be target biomaterials of the present invention.

Specific proteins include so called disease markers. Examples thereof include α-fetoprotein (AFP) being acidic glycoprotein produced by hepatic cells during the fetal period and existing in fetal blood, and serving as a marker for liver carcinoma (primary hepatic cancer), hepatoblastoma, metastatic liver cancer and yolk sac tumors, PIVKA-II being abnormal prothrombin appearing during hepatic parenchyma damage, and found to specifically appear in liver cell carcinoma, BCA225 being glycoprotein being a breast cancer specific antigen from an immunohistochemical viewpoint, and serving as a marker for primary advanced breast cancer and recurrent/metastatic breast cancer, basic fetoprotein (BFP) being a basic fetal protein found in human fetal serum, bowel and brain tissue extracts, and serving as a marker for ovary cancer, orchioncus, prostate cancer, pancreas cancer, biliary cancer, liver cell cancer, kidney cancer, lung cancer, gastric cancer, bladder cancer and large bowel cancer, CA15-3 being a polysaccharide antigen serving as a marker for advanced breast cancer, recurrent breast cancer, primary breast cancer and ovary cancer, CA19-9 being a polysaccharide antigen serving as a marker for pancreas cancer, biliary cancer, gastric cancer, liver cancer, large bowel cancer and ovary cancer, CA72-4' being a polysaccharide antigen serving as a marker for ovary cancer, breast cancer, colon/rectum cancer, gastric cancer and pancreas cancer, CA125 being a polysaccharide antigen serving as a marker for ovary cancer (particularly serous cyst cancer), uterine body cancer, uterine tube cancer, uterine cervix cancer, pancreas cancer, lung cancer and large bowel cancer, CA130 being glycoprotein serving as a marker for epidermal ovary cancer, uterine tube cancer, lung cancer, liver cell cancer and pancreas cancer, CA602 being core protein antigen serving as a marker for ovary cancer (particularly serous cyst cancer), uterine body cancer and uterine cervix cancer, CA54/61 (CA546) being a core polysaccharide related antigen serving as a marker for ovary cancer (particularly serous cyst cancer), uterine cervix cancer and uterine body cancer, a cancer fetal antigen (CEA) that is currently used most widely for aiding cancer diagnosis as a marker antigen related to large bowel cancer, gastric cancer, rectal cancer, biliary cancer, pancreas cancer, lung cancer, breast cancer, uterine cancer, urinary system cancer and he like, DUPAN-2 being a sugar antigen serving as a marker for pancreas cancer, biliary cancer, liver cell cancer, gastric cancer, ovary cancer and large bowel cancer, elastase 1 being a pancreatic outer secretion enzyme existing in pancreas and specifically hydrolyzing elastic fiber elastin of connective tissues (constituting arterial walls and tendons), and serving as a marker for pancreas cancer, cystic cancer and biliary cancer, immune suppression acidic protein (IAP) being glycoprotein existing in high concentrations in ascites and serum of a human cancer patient, and serving as a marker for lung cancer, leukemia, esophageal cancer, pancreas cancer, ovary cancer, kidney cancer, bile duct cancer, gastric cancer, bladder cancer, large bowel cancer, thyroidal cancer and malignant lymphoma, NCC-ST-439 being a polysaccharide antigen serving as a marker for pancreas cancer, biliary cancer, breast cancer, large bowel cancer, liver cell cancer, lung cancer and gastric cancer, γ-semino protein (γ-Sm) being glycoprotein serving as a marker for prostate cancer, a prostate specific antigen (PSA) being glycoprotein extracted from human prostate tissues, existing only in prostate tissues, and therefore serving as a marker for prostate cancer, prostate acidic phosphatase (PAP) being an enzyme hydrolyzing a phosphate under acidic pH, secreted from prostate, and used as a tumors marker for prostate cancer, nerve specific enolase (NSE) being a glycolysis system enzyme specifically existing in nerve cells and neuroendocrine cells, and serving as a marker for lung cancer (particularly small cell carcinoma of lung), neuroblastoma, nerve system tumors, pancreas island cancer, small cell carcinoma of esophagus, gastric cancer, kidney cancer and breast cancer, a squamous cancer related antigen (SCC antigen) being a protein extracted/purified from liver metastatic focus of uterine cervix squamous cancer, and serving as a marker for uterine cancer (cervix squamous cancer,), lung cancer, esophageal cancer, head cervical cancer and skin cancer, a sialyl Le$^x$-i antigen (SLX) being a polysaccharide antigen serving as a marker for pulmonary cancer, esophageal cancer, gastric cancer, large bowel cancer, rectal cancer, pancreas cancer, ovary cancer and uterine cancer, Span-1 being a polysaccharide antigen serving as a marker for pancreas cancer, biliary cancer, liver cancer, gastric cancer and large bowel cancer, a tissue polypeptide antigen (TPA) being a single-chain polypeptide serving as a marker for esophageal cancer, gastric cancer, rectal/colon cancer, breast cancer, liver cell cancer, biliary cancer, pancreas cancer, lung cancer and uterine cancer, and being useful particularly for estimation of advance cancer, precognition of recurrence and follow-up in combination with other tumors markers, a sialyl Tn antigen (STN) being a mother nucleic polysaccharide antigen serving as a marker for ovary cancer, metastatic ovary cancer, gastric cancer, large bowel cancer, biliary system cancer, pancreas cancer and lung cancer, CYFRA (cytokeratin) being a tumors marker effective for detection of non-small cell carcinoma of lung, especially squamous cancer of lung. Pepsinogen (PG) being an inactivated precursor of 2 types of pepsin (PG I/PG II) being an protein digestive enzyme secreted in gastric juice, and serving as a marker for gastric ulcer (particularly lower gastric ulcer), duodenal ulcer (particularly recurrent and intractable cases), Brunner's gland tumors, Zollinger-Ellison syndrome and acute gastritis, C-eractive protein (CRP) being an acute phase reactant protein changing in blood plasma with tissue disorder and infection, and indicating a high value if heart muscle sphacelates due to acute cardiac infarction and the like, serum amyloid A protein (SAA) being an acute phase reactant protein changing in blood plasma with tissue disorder and infection, myoglobin being a heme protein with the molecular weight of about 17500 mainly existing in heart muscle and skeletal muscle, and serving as a marker for acute cardiac infraction, muscle dystrophy, multiple myositis and skin myositis, creatine kinase (CK) (three types of isozyme: CK-MM type derived from skeletal muscle, CK-BB type derived from brain and smooth muscle, CK-MB type derived from cardiac muscle, as well as mitochondria isozymes and complex CK with immune globulin (macro CK)) being an enzyme existing mainly in soluble fractions of skeletal muscle and heart muscle and released into blood with damage of cells, and serving as a marker for acute cardiac infarction, hypothyroidism, advanced muscle dystrophy and multiple myositis, troponin T being a protein with the molecular weight of 39,000 forming a troponin complex with troponins I and C on a thin filament of stripped muscle and involved in regulation of muscle contraction, and serving as a marker for rhabdomyolysis, myocarditis, cardiac infarction and kidney failure, ventricular muscle myosin light chain I being a protein contained in cells of both skeletal muscle and cardiac muscle, indicating disorder and sphacelation of skeletal muscle and cardiac muscle by rise in measurement results, and therefore serving as a marker for acute cardiac infarction, muscle dystrophy and kidney failure, and chromogranin A, thioredoxin and 8-OhdG which have received attention as stress markers in recent years.

Detecting means in the present invention can be appropriately selected from known methods and used. For example, a substance that specifically recognizes or bind the target substance, for example an antibody (so called secondary antibody), labeled with a labeling compound, can be used for detection or quantitative determination. For example, such a secondary antibody is an antibody that bind to the target substance at a portion other than the portion recognized by the organic material of the present invention, and is desirably a monoclonal antibody, or a group of such monoclonal antibodies (polyclonal antibodies). For the labeling compound, fine particles of metals such as gold and organic material such as latex, fluorescent substances emitting fluorescence by excitation light in a specific wave range, and enzymes of which reaction products are fluorescent substances, e.g. HRP (horse radish peroxidase) are generally used. Methods for labeling proteins such as antibodies include a method by physical adsorption and a chemical binding method of introducing a functional group having a reaction activity into a target substance or non-target substance, and forming a chemical bond with the functional group as a cross-linking point.

Fluorescent substances include previously known 4-methylumbelliferone, 7-hydroxy-4-biphenyl-umbelliferone, 3-hydroxy-2-naphthoic acid 2-phenylanilide, 3-hydroxy-2-naphthoic acid-2,4-dimethylanilide, 6-bromo-2-hydroxy-3-naphthoic acid 2-methylalinide, 3-hydroxy-2-anthranoic acid 2-methylalinide, pyrene, fluorescein, perylene, rhodamine and texas red.

For the Luminescent substance, for example, luminal, luminal derivatives, luciferin, lucigenin and the like are used.

The Metal may be metal element-containing fine particles including any metal element such as an alkali metal such as gold, silver, copper, platinum, zinc, aluminum, lithium or aluminum, an alkali earth metal such as beryllium, magnesium or potassium, or a metal that is magnetized, such as iron, cobalt or nickel. Preferably, the metals include gold, silver, copper, aluminum, zinc and potassium that easily cause plasmon resonance, but they are not limited to these elements. Semiconductor fine particles include semiconductor nano particles such as ZnS, ZnSe, ZnTe, CdS, CdSe, CdTe, InGaAs and InP. Furthermore, they include not only fine particles formed of one semiconductor type, but also semiconductor fine particles covered with a semiconductor material having a wider band gap. The particle size of semiconductor fine particles may be preferably 1 to 50 nm, more preferably 2 to 20 nm. Ferromagnetic fine particles may include, for example, $Fe_3O_4$, $\gamma\text{-}Fe_2O_3$, $Co\text{-}\gamma\text{-}Fe_2O_3$, $(NiCuZn)O.Fe_2O_3$, $(CuZn)O.Fe_2O_3$, $(Mn.Zn)O.Fe_2O_3$, $(NiZn)O.Fe_2O_3$, $SrO.6Fe_2O_3$, $BaO.6Fe_2O_3$, $Fe_3O_4$ covered with $SiO2$, (particle size: about 200 A) [see Enzyme Microb. Technol., vol. 2, p. 2-10 (1980)], and conjugate fine particles of various kinds of polymer materials (nylon, polyacryl amide proteins, etc.) and ferrites.

EXAMPLES

The present invention will be described below more specifically with Examples. These Examples are examples of the best embodiments according to the present invention, but the present invention is not limited to them.

In Examples described below, a biomaterial-immobilizing substrate and a method for production of the same will be described specifically employing a polyhydroxyalkanate (PHA) synthetase protein as a biomaterial corresponding to the functional domain and a peptide having an affinity to the silicon oxide layer as a binding domain. A biomaterial-immobilizing substrate was made by immobilizing a fusion PHA synthetase protein, of which N-terminus had been ligated to a peptide having an affinity to silicon oxide layer through a linker sequence, on a substrate covered with a silicon oxide layer.

Also a method for obtaining peptides having an affinity to the silicon oxide layer, which is used as the above-described binding domain, will be described specifically.

In advance to Examples, a method for forming a silicon oxide layer, specifically a mesoporous silica (SBA-15) layer that is used in the above-described biomaterial immobilizing substrate will be described in Reference Example 1, and methods for genetic recombination production of the PHA synthetase protein, the enzyme activity determination of the recombinant PHA synthetase protein will be described in Reference Example 2.

Further, in Examples, the enzyme activity of the immobilized fusion PHA synthetase on the silicon oxide layered substrate is estimated in comparison with that of the free recombinant PHA synthetase protein.

Reference Example 1

Preparation of Mesoporous Silica (SBA-15)

A silica reaction solution consisting of 4 g of poly (ethylene oxide)-poly (propylene oxide)-poly (ethylene oxide) block copolymer comprised of 20 units of ethylene oxide, 70 units of propylene oxide and 20 units of ethylene oxide, hereinafter referred to as $EO_{20}$-$PO_{70}$-$EO_{20}$, 0.041 mol tetraethoxy silane (TEOS), 0.24 mol HCl and 6.67 mol $H_2O$ was prepared.

This silica reaction solution was reacted at 35° C. for 20 hours, and then at 80° C. for 48 hours. Subsequently, the solution was heated at 500° C. for 6 hours to burn out the contained block copolymer $EO_{20}$-$PO_{70}$-$EO_{20}$, whereby porous silica was obtained.

In the obtained porous silica, the average pore size was 7.9 nm, the average thickness of the silica wall between the pores was 3 nm.

Reference Example 2

Preparation of Transformant Having Capability of Producing PHA Synthetase, and Production of PHA Synthetase A transformant having a capability of producing a PHA synthetase was prepared as follows.

First, Strain YN2 (Pseudomonas cichorii YN2, FERM BP-7375) having a capability of producing a PHA synthetase was cultured in 100 ml of LB culture medium (1% polypeptone, 0.5% yeast extract, 0.5% sodium chloride, pH 7.4) at 30° C. overnight, and then chromosomal DNA of the Strain YN2 was separated and collected by the method of Marmur, et al. The obtained chromosomal DNA was fully digested by a restriction enzyme HindIII. A cloning vector pUC18 was cleaved with the restriction enzyme HindIII. After terminal dephosphorylation (Molecular Cloning, 1, 572 (1989); Cold Spring Harbor Laboratory Press.), a DNA ligation kit Ver. II (Takara Shuzo Co., Ltd.) was used to insert/ligate the HindIII digested fragments of the chromosomal DNA into the cleaved site (cloning site) of the vector. With the plasmid vectors having the chromosomal DNA fragments incorporated therein, Escherichia coli HB101 was transformed to prepare a DNA library of Strain YN2.

Then, for selecting DNA fragments containing the PHA synthetase gene derived from Strain YN2, a colony hybridization probe was prepared. Oligonucleotides having base sequences of SEQ ID NOS: 11 and 12 were synthesized (Amersham Pharmacia Biotech), and these two types of oligonucleotides were used as a primer set for PCR amplification using chromosomal DNA as a template. The PCR amplification product was isolated, and used as a colony hybridization probe. The probe was labeled utilizing a commercially available alkali phosphatase labeling kit, AlkPhos-Direct (Amersham Pharmacia Biotech). The obtained enzyme-labeled probe was used to select strains harboring a recombinant plasmid containing a desired PHA synthetase gene from the chromosomal DNA library by the colony hybridization method. Collecting the plasmid from the selected strain by the alkali method, DNA fragments containing the PHA synthetase gene derived from Strain YN2 were obtained.

(SEQ ID NO: 11) Base sequence of forward primer
5'-TGCTGGAACT GATCCAGTAC-3'

(SEQ ID NO: 12) base sequence of forward primer
5'-GGGTTGAGGA TGCTCTGGAT GTG-3'

The PHA synthetase gene DNA fragment obtained here was cloned into vector pBBR122 (Mo Bi Tec) having a wide-host-replication range not belonging to any of incompatibility groups of IncP, IncQ and IncW. This recombinant plasmid was transformed into Pseudomonas cichorii YN2 ml strain (a PHA synthesis defective strain) by the electroporation method and as a result, the PHA synthesis capability was restored showing complementarity in the transformed YN1ml strain. Thus, it is shown that the selected gene DNA fragment contains a PHA synthetase gene region capable of being translated into a PHA synthetase at least in Pseudomonas cichorii YN2 ml.

For the DNA fragment containing the PHA synthetase gene derived from the Strain YN2, the base sequence was determined by the Sanger's method. As a result, it was found out that two types of base sequences were present in the determined base sequence, that is, SEQ ID NO: 7 and SEQ ID NO: 8, each encoding a peptide chain. As described below, two types of peptide chains encoded by these two types of base sequences each had PHA synthetase activity, and the base sequences expressed by SEQ ID NO: 7 and SEQ ID NO: 8 were PHA synthetase genes, respectively. That is, the base sequence of SEQ ID NO: 7 encodes the amino'acid sequence expressed by SEQ ID NO: 9, and the base sequence of SEQ ID NO: 8 encodes the amino acid sequence expressed by SEQ ID NO: 10, and each protein having one of these amino acid sequences can exhibit the PHA synthesis activity.

For the PHA synthetase gene of SEQ ID NO: 7, PCR amplification was performed with chromosomal DNA as a template to obtain a full length PHA synthetase gene.

For the base sequence expressed by SEQ ID NO: 7, an oligonucleotide (SEQ ID NO: 15) having a base sequence present upstream the initiation codon was designed and synthesized as the upstream primer, and an oligonucleotide (SEQ ID NO: 13) having a base sequence present downstream the termination codon was designed and synthesized as the downstream primer (Amersham Pharmacia Biotech). Using the two types of oligonucleotides as a primer pair, PCR amplification was performed with chromosomal DNA as a template to amplify the full length PHA synthetase gene (LA-PCR kit; Takara Shuzo Co., Ltd.).

(SEQ ID NO: 15) base sequence of upstream primer
5'-GGACCAAGCT TCTCGTCTCA GGGCAATGG-3'

(SEQ ID NO: 13) base sequence of downstream primer
5'-CGAGCAAGCT TGCTCCTACA GGTGAAGGC-3'

Similarly, PCR amplification was performed with chromosomal DNA as a template to obtain the full length PHA synthetase gene having a base sequence of SEQ ID NO: 8. For the base sequence expressed by SEQ ID NO: 8, an oligonucleotide (SEQ ID NO: 14) having a base sequence present upstream the initiation codon was designed and synthesized as the upstream primer, and an oligonucleotide (SEQ ID NO: 16) having a base sequence downstream the termination codon as the downstream primer (Amersham Pharmacia Biotech). Using the oligonucleotides as a primer set, PCR was performed to amplify the full length of the PHA synthetase gene (LA-PCR kit; Takara Shuzo Co., Ltd.).

(SEQ ID NO: 14) base sequence of upstream primer
5'-GTATTAAGCT TGAAGACGAA GGAGTGTTG-3'

(SEQ ID NO: 16) base sequence of downstream primer
5'-CATCCAAGCT TCTTATGATC GGGTCATGCC-3'

Next, the obtained PCR amplified fragment and an expression vector pTrc99A were digested by the restriction enzyme HindIII and dephosphorylated (Molecular Cloning, vol. 1, p. 572, (1989); Cold Spring Harbor Laboratory Press), then the DNA fragment including a full length PHA synthetase gene excluding unnecessary base sequences at both terminuses was linked to a restriction site of the expression vector pTrc99A by using a DNA ligation kit Ver. II (TAKARA SHUZO CO., LTD.).

An *E. coli* strain (*Escherichia coli* HB101: TAKARA SHUZO) was transformed with each of the obtained recombinant plasmids by the calcium chloride method. The obtained recombinants were cultured and the recombinant plasmids were amplified, then the recombinant plasmids were respectively recovered. The recombinant plasmid having a full length PHA synthetase gene of SEQ ID NO: 7 was designated as pYN2-C1 (obtained with SEQ ID NO: 11), and the recombinant plasmid having a full length PHA synthetase gene DNA of SEQ ID NO: 8 was designated as pYN2-C2 (obtained with SEQ ID NO: 12).

An *E. coli* strain (*Escherichia coli* HB101fB fadB deletion strain) was transformed with pYN2-C1 and pYN2-C2 respectively by the calcium chloride method to obtain recombinant *E. coli* strains having respective recombinant plasmids, i.e., a pYN2-C1 recombinant strain and a pYN2-C2 recombinant strain.

The recombinant strains pYN2-C1 and pYN2-C2 were each planted in 200 ml of M9 culture medium containing 0.5% of yeast extract and 0.1% of octanoic acid, and cultured at 37° C. with shaking at 125 strokes/minute. After 24 hours, cells were collected by centrifugation, and plasmid DNA was collected by a conventional method. For the pYN2-C1, an upstream primer (SEQ ID NO: 17) and a downstream primer (SEQ ID NO: 18) were designed and synthesized respectively (Amersham Pharmacia Biotech). PCR was carried out with LA-PCR kit (TAKARA SHUZO CO., LTD.) using these primers and template pYN2-C1 to synthesize a full-length PHA synthetase gene having BamHI and SacI restriction sites upstream and SpeI and XhoI restriction sites downstream.

```
Upstream primer (SEQ ID NO: 17):
5'-AGTGGATCCT CCGAGCTCAG TAACAAGAGT AACGATGAGT

TGAAG-3'

Downstream primer (SEQ ID NO: 18):
5'-ATACTCGAGA CTACTAGTCC GTTCGTGCAC GTACGTGCCT

GGCGC-3'
```

Similarly, for pYN2-C2, an upstream primer (SEQ ID NO: 19) and a downstream primer (SEQ ID NO: 20) were designed and synthesized respectively (Amersham Pharmacia Biotech). PCR was carried out with an LA-PCR kit (TAKARA SHUZO CO., LTD.) using these primers and the template pYN2-C2 to amplify the full length PHA synthetase gene having a BamHI restriction site upstream and a XhoI restriction site downstream.

```
Upstream primer (SEQ ID NO: 19):
5'-ATACTCGAGA CTACTAGTGC GCACGCGCAC GTAAGTCCCG

GGCGC-3'

Downstream primer (SEQ ID NO: 20):
5'-AGTGGATCCT CCGAGCTCCG CGATAAACCT GCGAGGGAGT

CACTA-3'
```

The purified PCR amplification products were digested with restriction enzymes BamHI and XhoI, and inserted into the corresponding site of the plasmid pGEX-6P-1 (Amersham Pharmacia Biotech). Using the two types of vectors (pGEX-C1 and pGEX-C2), an *E. coli* strain JM109 was transformed to obtain strains for expression. To confirm introduction of the expression vector in each strain, the plasmid DNA was prepared by Miniprep (Wizard Minipreps DNA-Purification Systems, PROMEGA) in a large amount and digested by BamHI and XhoI, and the resulting DNA fragment was identified. The PHS synthetase was expressed and purified as follows: The obtained strain was pre-cultured in 10 ml of LB-Amp medium overnight, and then an 0.1 ml culture was transferred to 10 ml of LB-Amp medium and cultured at 37° C., 170 rpm for 3 hours with shaking. Then, IPTG was added to the culture to a concentration of 1 mM, then the culture was continued for 4 to 12 hours at 37° C.

The *E. coli* cells induced with IPTG were collected (8,000× g, 2 min., 4° C.) and re-suspended in a ¹/₁₀ volume of phosphate buffer physiological saline (PBS; 8 g NaCl, 1.44 g $Na_2HPO_4$, 0.24 g $KH_2PO_4$, 0.2 g, KCl, 1,000 ml purified water) at 4° C. The cells were disrupted by freeze and thawing and sonication, and subjected to centrifugation (8,000×g, 10 min., 4° C.) to remove solid impurities. Confirming that the aimed recombinant protein was present in the supernatant by SDS-PAGE, the induced and expressed GST fusion protein was purified by using Glutathione Sepharose 4B (Amersham Pharmacia Biotech).

The Glutathione Sepharose was previously treated to avoid nonspecific adsorption, that is, the Glutathione Sepharose was washed with an equivalent amount of PBS for three times (8,000×g, 1 min., 4° C.), and then an equivalent amount of 4% bovine serum albumin PBS was added thereto at 4° C. for one hour. After that, the Sepharose was washed with an equivalent amount of PBS twice, and re-suspended in an ½ amount of PBS. The pre-treated 40 µl of Glutathione Sepharose was added to 1 ml of the above cell free extract, and gently stirred at 4° C. to adsorb fusion protein GST-YN2-C1 and GST-YN2-C2 onto Glutathione Sepharose respectively. After centrifugation (8,000×g, 1 min., 4° C.) to collect the Glutathione Sepharose, it was washed with 400 µl of PBS for three times.

After the washing, 10 mM of glutathione was added thereto and stirred for one hour at 4° C. to elute the adsorbed fusion protein. After centrifugation (8,000×g, 2 min., 4° C.), the supernatant was recovered and dialyzed against PBS to purify the GST fusion protein. Single band was recognized by SDS-PAGE.

Then 500 µg of each GST fusion protein was digested by PreScission protease (Amersham Pharmacia Biotech, 5 U), the protease and the GST were removed therefrom by passing through Glutathione Sepharose. The flow-through fraction was further loaded to Sephadex G200 column equilibrated with PBS, then expression proteins YN2-C1 and YN2-C2 were obtained as final purified products. By SDS-PAGE, single bands (60.8 kDa and 61.5 kDa, respectively) were confirmed.

The activity of each purified enzyme protein was measured by the following method the following method that measures CoA released from 3-hydroxyacyl CoA during PHA polymerization reaction catalyzed by PHA synthetase utilizing color development with 5,5'-dithiobis-(2-nitrobenzoic acid): Reagent 1: a 3.0 mg/ml solution of bovine serum albumin (Sigma) dissolved in 0.1 M Tris-HCl buffer (pH 8.0), Reagent 2: a 3.0 mM solution of 3-hydroxyoctanoyl CoA in 0.1 M Tris-HCl buffer (pH 8.0); Reagent 3: a 10 mg/ml solution of trichloroacetic acid in 0.1 M Tris-HCl buffer (pH 8.0), Reagent 4: a 2.0 mM solution of 5,5'-dithiobis-(2-nitrobenzoic acid) in 0.1 M Tris-HCl buffer (pH 8.0).

First reaction (PHA synthesizing reaction): 100 μl of Reagent 1 is added to and mixed with 100 μl of the sample (enzyme) solution, then the mixture is pre-incubated for one minute at 30° C., to which 100 μl of Reagent 2 is added and mixed. The resultant mixture is incubated for 1 to 30 minutes at 30° C. and the reaction is stopped by adding Reagent 3.

Second reaction (color development of free CoA): The resulting first reaction solution is centrifuged (15,000×g, for 10 minutes). To 500 μl of the supernatant, 500 μl of Reagent 4 is added and incubated for 10 minutes at 30° C. Then the absorbance at 412 nm is measured.

Calculation of enzyme activity: The amount of enzyme that releases 1 μmol of CoA within one minute is defined as one unit (U).

The concentration of the protein in the sample was measured by using Micro BCA Protein Quantitative Reagent Kit (manufactured by Pierce Chemical Co., Ltd.). The results of measurement of activities of the purified enzymes are shown in Table 1.

TABLE 1

| PHA synthetase | Activity | Specific activity |
|---|---|---|
| YN2-C1 | 2.1 U/ml | 4.1 U/mg protein |
| YN2-C2 | 1.5 U/ml | 3.6 U/mg protein |

The above-described enzymes were concentrated with a bioliquid concentrating agent (Mizubutorikun AB-1100, Atto Corp.) to obtain 10 U/ml of purified enzyme solutions. In Examples shown below, PHA synthetase protein YN-C1 having a higher specific activity was used.

Example 1

Acquirement of Amino Acid Sequence Having an affinity for Mesoporous Silica (SBA-15)

(Step 1)

The mesoporous silica SBA-15 described in Reference Example 1 was suspended in a 0.1% Tween-20/TBS buffer (50 mM Tris-HCl pH 7.5, 150 mM NaCl) (hereinafter referred to as TBST buffer) at a concentration of 5 mg/ml. 10 μl of the suspension was added to an Eppendorf tube, and 990 μl of TBST buffer (TBS buffer+0.1% Tween-20) was added to dilute the suspension.

(Step 2)

$4 \times 10^{10}$ pfu equivalent of the PhD. –12 phage display peptide library (NEW ENGLAND BIOLAB) was added to the above-described tube, and left standing at 25° C. for 30 minutes.

(Step 3)

The above-described tube was subjected to centrifugal separation (20, 630×g, 5 minutes), and then the supernatant was discarded to collect SBA-15 as a pellet. The pellet was re-suspended in TBST buffer. By repeating this operation of centrifugation and re-suspension, the SBA-15 was washed with the TBST buffer ten times.

(Step 4)

100 μl of elution buffer (0.2 M glycine-HCl (pH 2.2), 1 mg/ml BSA) was added to the washed SBA-15, the mixture was gently shaken for 10 minutes, and then subjected to centrifugal separation (20,630×g, 5 minutes), and the supernatant was transferred to another Eppendorf tube, to which 15l of 1 M Tris-HCl (pH 9.1) was added to neutralize it. Thus phages eluted from above the SBA-15 were obtained.

(Step 5)

For amplification, the eluted phage was used to infect E. coli ER2537 (NEW ENGLAND BIOLAB Co., Ltd.) in its early logarithmic growth phase according to the following procedures.

The infected E. coli cells were cultured at 37° C. for 4.5 hours. Then, the phage particles were separated from E. coli cells by centrifugal separation, precipitated from the supernatant with polyethylene glycol, and purified. The amplified and purified phage was suspended in the TBS buffer and diluted in a dilution series, and the dilutions were used to infect E. coli cells for titer determination (SBA-15 binding (C)).

(Step 6)

Using the phages obtained by the first screening above, the screening operation of the above-described steps 1 to 5 was repeated four times regarding the affinity for mesoporous silica SBA-15, except that in the subsequent screening the concentration of Tween-20 in the TBST buffer used for washing was increased to 0.5%, making washing conditions in step 3 more strict to select phages having higher affinity for mesoporous silica SBA-15. Furthermore, in the subsequent screening (2nd to 5th screening), the titer of the phage eluted from SBA-15 in the step 3 was determined in the same manner, to use it as the control binding (B).

The titers of phages eluted from SBA-15 in the first to fifth screenings as described above are shown in Table 2.

TABLE 2

| | Titer of phage eluted in each round of screening | | | | |
|---|---|---|---|---|---|
| | Stock solution (A) | Control binding (B) | SBA-15 binding (C) | C/A | C/B |
| First round | $1.0 \times 10^{10}$ | | $2.3 \times 10^{4}$ | $2.3 \times 10^{-6}$ | |
| Second round | $1.0 \times 10^{11}$ | $2.3 \times 10^{3}$ | $1.9 \times 10^{4}$ | $1.9 \times 10^{-7}$ | 8 |
| Third round | $1.0 \times 10^{11}$ | $1.0 \times 10^{3}$ | $4.2 \times 10^{4}$ | $4.2 \times 10^{-7}$ | 42 |
| Fourth round | $1.0 \times 10^{11}$ | $2.0 \times 10^{1}$ | $1.2 \times 10^{5}$ | $1.2 \times 10^{-6}$ | $6.0 \times 10^{3}$ |
| Fifth round | $1.0 \times 10^{11}$ | $1.0 \times 10^{1}$ | $2.2 \times 10^{6}$ | $2.2 \times 10^{-5}$ | $2.2 \times 10^{4}$ |

(The unit for A, B and C is pfu/μl)

The selected phages, those eluted in the final screening step, were cloned by making them infect excessive E. coli cells.

Each isolated clone was amplified in E. coli, and ssDNA was prepared from each phage clone, and the base sequence of the random domain was determined to identify 15 phage clones having high affinity for SBA-15.

For the obtained 15 phage clones, the affinity for silicon oxide was evaluated by the phage ELISA, and the DNA encoding the displayed peptide portion of each phage was sequenced to determine the amino acid sequence of the peptide capable of binding to silicon oxide.

1) Evaluation of Affinity for Silicon Oxide by Phage ELISA (Step 1)

BA-15 was suspended in a 0.1% Tween-20/TBS buffer (50 mM Tris-HCl pH 7.5, 150 mM NaCl) (hereinafter referred to as TBST) at a concentration of 5 mg/ml. 10 μl of the suspension was added to each Eppendorf tube, and 990 μl of TBST buffer (TBS buffer+0.1% Tween-20) was added to dilute the suspension.

(Step 2)

$4 \times 10^{10}$ pfu suspension of each phage of the above 15 phage clones selected from the PhD. -12 phage display peptide library (NEW ENGLAND BIOLAB) was added to the above-described tube, and left standing at 25° C. for 30 minutes.

(Step 3)

The above-described tube was subjected to centrifugal separation (20, 630×g, 5 minutes), and then the supernatant was discarded to collect SBA-15 as a pellet. The pellet was re-suspended in TBST buffer. By repeating this operation of centrifugation and re-suspension, the SBA-15 was washed with the TBST buffer ten times.

(Step 4)

100 μl of HRP-bound anti-M13 antibody solution (prepared by suspending 1 μL of HRP-anti-M13 antibody (manufactured by NEW ENGLAND BIOLAB Co., Ltd.) in 10 mL of TBST) was added to washed SBA-15 in the above tube, and gently shaken for 60 minutes. Then, the tube was subjected to centrifugal separation (20, 630×g, 5 minutes), and the supernatant was discarded to collect SBA-15 as a pellet. The pellet was re-suspended in TBST buffer. By repeating this operation of centrifugation and re-suspension, the SBA-15 was washed with the TBST buffer five times.

(Step 5)

The above phage on the SBA-15 reacted with the above-described HRP binding anti-M13 antibody was suspended with 50 μL of Reaction Reagent 1 (Amersham Pharmacia #RPN2209) and placed in a well of a 96 well titer plate.

Further, 50 μL of detection reagent 2 (Amersham Pharmacia #RPN2209) was added and after 3 minutes, the luminol light emission intensity obtained with the action of the labeling HRP enzyme in the HRP anti-M13 antibody was measured at 428 nm.

The evaluation results for the clones are shown in Table 3. $I_{420}$ represents the light emission intensity at 420 nm.

TABLE 3

Results of evaluation of affinity for silicon oxide by phage ELISA

| | Clone No | | | | | | | |
|---|---|---|---|---|---|---|---|---|
| | 1 | 2 | 3 | 4 | 5 | 6 | 7 | 8 |
| $I_{420}$ | 0.452 | 0.881 | 0.336 | 0.229 | 0.377 | 0.433 | 0.555 | 0.326 |

| | Clone No | | | | | | |
|---|---|---|---|---|---|---|---|
| | 9 | 10 | 11 | 12 | 13 | 14 | 15 |
| $I_{420}$ | 0.132 | 0.498 | 0.543 | 0.198 | 0.478 | 0.299 | 0.364 |

Furthermore, in the above phage ELISA measurement system, the light emission intensity observed when no phage was contacted with SBA-15 (control) in step 2 was 0.0009.

It was shown by the above evaluation that all peptides displayed by 15 phage clones obtained had affinity for silicon oxide.

2) Amino Acid Sequence Exhibiting Capability of Binding to Silicon Oxide

For the selected 15 phage clones, amino acid sequences of displayed peptides deduced from the DNA sequence analysis were compared to identify the amino acid sequence participating in affinity for silicon oxide. The identified amino acid sequences having an affinity for silicon oxide and their occurrence frequency are shown in Table 4.

TABLE 4

Determined amino acid sequences and occurrence frequency

| Determined amino acid sequences | Number (A) | Frequency (A/15) |
|---|---|---|
| Val-Ser-Pro-Met-Arg-Ser-Ala-Thr-Thr-His-Thr-Val SEQ ID NO: 1 | 13 | 0.86 |
| Ile-Pro-Met-His-Val-His-His-Lys-His-Pro-His-Val SEQ ID NO: 2 | 2 | 0.14 |

Example 2

A PHA synthetase containing a fused peptide having an affinity to the above-described SBA-15 was prepared as follows.

E. coli expression vectors were constructed in the following manner, each encoding a PHA synthetase fusion having an amino acid sequence SEQ ID NO: 1 or SEQ ID NO: 2 having SBA-15 affinity obtained in Example 1, at N-terminus of the PHA synthetase through a linker sequence GGGS. For preparing dsDNA fragments encoding the affinity amino acid sequences, a set of synthetic oligonucleotides having base sequences shown in Table 5 was prepared.

TABLE 5

Synthetic DNA set for expressing peptide chains of amino acid sequences

| SEQ ID NO: amino acid sequence | SEQ ID NO: base sequence of synthetic DNA |
|---|---|
| 1:VSPMRSATTHTV | 3: 5'-GATCCGTGAGCCCCATGAGGAGCGCCACCACCCACACCGTGGGTGGAGGTTCGGAGCT-3'<br>4: 5'-CGAACCTCCACCCACGGTGTGGGTGGTGGCGCTCCTCATGGGGCTCAC-3' |
| 2:IPMHVHHKHPHV | 5: 5'-GATCCATCCCCATGCACGTGCACCACAAGCACCCCCACGTGGGTGGAGGTTCGGAGCT-3'<br>6: 5'-CGAACCTCCACCCACGTGGGGGTGCTTGTGGTGCACGTGCATGGGGAT-3' |

Two synthetic DNA fragments shown in Table 5 corresponding to one of the amino acid sequences were phosphorylated at the terminus using T4 polynucleotide kinase (manufactured by Gibco) according to the instruction manual of the manufacturer. Subsequently, they were mixed together in an equimolar ratio, heated at 80° C. for 5 minutes, and then slowly cooled to room temperature to form a double-stranded DNA fragment. The formed dsDNA fragment was used directly for subsequent recombination.

The plasmid pGEX-C1 prepared in Reference Example 2 was digested with restriction enzymes BamHI and SacI, and the above-described dsDNA was inserted therein. E. coli JM109 was transformed with the vector to obtain recombinants expressing a fusion. Introduction of the expression vector in each strain was confirmed by determining the base sequence inserted between the BamHI and SacL restriction sites using pGEX 5' Sequencing Primer (manufactured by Amersham Pharmacia Biotech Co., Ltd.) and the plasmid DNA prepared using Miniprep (Wizard Minipreps DNA Purification Systems manufactured by PROMEGA Co., Ltd.) as a template. The obtained expression strain was precultured in 10 mL of LB-Amp culture medium overnight, and then 0.1 mL of the culture was added to 10 mL of fresh LB-Amp culture medium, and cultured at 37° C. for 3 hours with shaking at 170 rpm. Thereafter, IPTG (final concentration of 1 mM) was added, and culture was continued at 37° C. for 4 to 12 hours.

IPTG-induced *E. coli* was collected (8000×g, 2 minutes, 4° C.), and re-suspended in PBS (4° C.) of 1/10 amount. Cells were disrupted by freeze and thawing and sonication, and centrifuged (8000×g, 10 minutes, 4° C.) to remove solid contaminants. Existence of the expressed target protein (GST fusion protein) in the supernatant was confirmed by SDS-PAGE. Then the induced/expressed GST fusion protein in the supernatant was purified with glutathione sepharose 4B (Glutathion Sepharose 4B beads manufactured by Amersham Pharmacia Biotech Co., Ltd.). One GST fusion protein was a fusion protein GST-01-YN2-C1 having a peptide of SEQ ID NO: 1 and the linker GGGS between the C-terminus of the GST protein and the N-terminus of the PHA synthetase protein YN2-C1, and the other was a fusion protein GST-02-YN2-C1 having a peptide chain of the above SEQ ID NO: 2 and the linker GGGS inserted between the C-terminus of the GST protein and the N-terminus of the PHA synthetase protein YN2-C1.

The glutathione sepharose used was previously subjected to a treatment to prevent nonspecific adsorption. That is, the glutathione sepharose was washed with an equal amount of PBS three times (8000×g, 1 minute, 4° C.), and then an equal amount of PBS containing 4% BSA was added to carry out a treatment at 4° C. for 1 hour. After the treatment, the glutathione sepharose was washed twice with an equal amount of PBS, and re-suspended in an equal amount of PBS to the glutathione sepharose. 40 μl of pretreated glutathione sepharose was added to 1 ml of cell-free extract (supernatant), and gently stirred at 4° C. By this stirring, the fusion protein GST-01-YN2-C1 or GST-02-YN2-C1 was adsorbed to glutathione sepharose.

After adsorption, glutathione sepharose was collected by centrifugation (8000×g, 1 minute, 4° C.), and washed with 400 μL of PBS three times. Thereafter, 40 μL of 10 mM glutathione was added, and stirred at 4° C. for 1 hour to elute the fusion protein. The supernatant containing the fusion protein was collected by centrifugation (8000×g, 2 minutes, 4° C.), and then the GST fusion protein was purified by dialysis with PBS. After purification, SDS-PAGE confirmed that the protein migrated as a single band.

500 μg of each GST fusion protein was digested with PreScission protease (Amersham Pharmacia Biotech, 5 U) to cut off the fused partner GST portion at the N-terminus. This solution was passed through a glutathione sepharose column to remove protease and GST. Then the flow-through fraction from the glutathione sepharose column was passed through a Sephadex G200 column equilibrated with PBS to obtain a final purified product of a peptide fusion protein 01-YN2-C1 or 02-YN2-C2. SDS-PAGE confirmed that the purified expression proteins 01-YN2-C1 and 02-YN2-C2 each migrated as a single band.

For the purified expression proteins 01-YN2-C1 and 02-YN2-C2 thus obtained, the enzyme activity was measured by the method described in Reference Example 2. The protein concentration of the sample was measured by Micro BCA Protein Quantitative Reagent Kit (manufactured by Pierce Chemical Co., Ltd.). The enzyme activity of the sample was 1.9 U/ml, and the specific activity was 4.0 U/mg protein. The finally purified enzyme solution was condensed using a biomaterial solution-condensing agent (Mizubutorikun AB-1100 manufactured by ATTO Co., Ltd.) to obtain a 10 U/ml purified enzyme solution.

Example 3

Evaluation of SBA-15 Affinity of Fusion Proteins 01-YN2-C1 and 02-YN2-C2

SBA-15 was suspended in a 0.1% Tween-20/TBS buffer in a concentration of 0.5% (w/v). 0.5 U equivalent of the peptide fusion PHA synthetases 01-YN2-C1, 02-YN2-C1 prepared in Example 2, the PHA synthetase YN2-C1 prepared in Reference Example 2 were respectively added to Teflon centrifugation tubes each containing a 10 ml aliquot of the SBA-15 suspension, and the tubes were shaken at room temperature for 30 minutes. By centrifugal separation operation (10,000× g, 4° C., 10 minutes), SBA-15 particles were collected as a pellet, and separated from the supernatant containing enzyme proteins that had not bound to SBA-15. Collected SBA-15 was washed by repeating the operation of suspending it in the TBS buffer containing 0.1% Tween-20 and centrifuging it. Table 6 shows the results of the enzyme activity measurement of the washed suspensions of SBA-15 according to the method described in Reference Example 2.

TABLE 6

Enzyme activity of each PHA synthetase protein bound on SBA-15

| PHA synthetase | Peptide having an affinity for silicon oxide | Enzyme activity U |
|---|---|---|
| 01-YN2-C1 | 1:VSPMRSATTHTV | 0.07 |
| 02-YN2-C1 | 2:IPMHVHHKHPHV | 0.06 |
| YN2-C1 | — | 0.01 |

It was shown that the enzyme proteins 01-YN2-C1 and 02-YN-C1 each having an SBA-15-binding peptide at the N-terminus had high enzyme activity compared with the enzyme protein YN2-C1 as a control, and the enzyme protein could be effectively immobilized on the substrate surface made of silicon oxide through the SBA-15-binding peptide fused to the N-terminus.

Example 4

An *E. coli* expression vector encoding a fusion protein in which both of two types of amino acid sequences having an affinity for SBA-15: Val-Ser-Pro-Met-Arg-Ser-Ala-Thr-Thr-His-Thr-Val (SEQ ID NO: 1) and Ile-Pro-Met-His-Val-His-His-Lys-His-Pro-His-Val (SEQ ID NO: 2) are linked in tandem via a spacer sequence of Gly-Gly-Gly-Ser-Gly-Gly-Gly-Ser to obtain a sequence of Val-Ser-Pro-Met-Arg-Ser-Ala-Thr-Thr-His-Thr-Val-Gly-Gly-Gly-Ser-Gly-Gly-Gly-Ser-Ile-Pro-Met-His-Val-His-His-lys-His-Pro-His-Val (SEQ ID NO: 21), and then linked to the N-terminus of PHA synthetase via a linker GS. The process was as follows.

DNA encoding the amino acid sequence of SEQ ID NO: 21 and the linker sequence GS was formed as a double-stranded DNA fragment by: first phosphorylating two types of synthetic oligonucleotides:

```
                                                    (SEQ ID NO: 22)
5'-GATCCGTGAGCCCCATGAGGAGCGCCACCACCCACACCGTGCGGCGG

CGGCAGCGGCGGCGGCAGCATCCCCATGCACGTGCACCACAAGCACCCCC

ACGTGGGAGCTGAGCT-3'
and
                                                    (SEQ ID NO: 23)
5'-AGCTCCCACGTCGGGGTGCTTGTGGTGCACGTGCATGGGGATCTGCC

GCCGCCGCTGCCGCCGCCGCACGGTGTGGGTGGTGGCGCTCCTCATGGGG

CTCAC-3'
``` at the terminus using T4 polynucleotide kinase (manufactured by Gibco), then mixing the synthetic oligonucleotides in an equimolar ratio, and heating at 80° C. for 5 minutes, followed by slow cooling to room temperature. The formed double-stranded fragment was inserted into the BamHI/SacI site of the plasmid pGEX-C1 in the same manner as in Example 2, and this vector was used to transform E. coli JM1109 to obtain a an expression strain. In the same manner as in Example 2, an expression protein 21-YN2-C1 having at the N-terminus a peptide (SEQ ID NO: 21) and the linker sequence GS was purified. A 10 U/ml purified enzyme solution was obtained. In the same manner as in Example 3, the enzyme activity of the enzyme protein bound on SBA-15 was measured to evaluate the affinity of the purified enzyme protein for SBA-15. The measurement results are shown in Table 7.

TABLE 7

Enzyme activity of each PHA synthetase protein bound on SBA-15

| PHA synthetase | Peptide having an affinity for silicon oxide | Enzyme activity U |
|---|---|---|
| 21-YN2-C1 (cb) | 21: VSPMRSATTHTVGGGSGGGSIPMHVHHKHPHV | 0.16 |
| YH2-C1 | — | 0.01 |

It was shown that the enzyme protein 21-YN2-C1 having on its N-terminus a peptide in which two amino acid sequences capable of binding to SBA-15 were fused had high enzyme activity in comparison with the enzyme protein YN2-C1 as a control, indicating that the enzyme protein was more effectively immobilized on the substrate surface made of silicon oxide through the N-terminus SBA-15-binding peptide.

Example 5

Example 5 is one example of an organic material-immobilizing structure and a method for production of the same, in which a recombinant polyhydroxyalkanoate (PHA) synthetase having affinity to silicon oxide layer is immobilized on a silicon substrate covered with a silicon oxide layer. FIG. 1 is a sectional view schematically showing the configuration of the organic material-immobilizing structure of Example 5.
(1) Preparation of Substrate Having Porous Silica Coating Layer A silicon substrate was used as a substrate 11 in the organic material-immobilizing structure of Example 5.

First, an SBA-15 reaction solution prepared in the same manner as in Reference Example 1 was applied onto a silicon substrate by a spin coater. The heating conditions for preparation of mesoporous silica (SBA-15) coating layer were the same as in Reference Example 1. By this method, a mesoporous silica film having an average thickness of 100 nm was formed on the silicon substrate 11.

It was confirmed that the mesoporous silica (SBA-15) film formed on the silicon substrate 11 would not fall off from the substrate surface even if it was washed with a TBS buffer (50 mM Tris-HCl (pH 7.5), 150 mM NaCl) containing 0.1% Tween-20. Through the step described above, a silicon substrate coated with SBA-15 (hereinafter referred to as a silica coated substrate in Example 5) was prepared, where the surface of the silicon substrate 11 was covered with the silicon oxide layer 12 composed of SBA-15.
(2) Evaluation of Affinity for Silica Coated Substrate Using the PHA synthetase protein 01-YN2-C1 having amino acid sequence of SEQ ID NO: 1 at the N-terminus, which was obtained as described in Example 2, the following evaluation was made.

30 ml of the silica-coated substrate prepared in the above step (1) was immersed in TBS buffer in a dish. A 2.5 U equivalent of the PHA synthetase protein 01-YN2-C1 prepared in Example 2 or the PHA synthetase protein YN2-C1 prepared in Reference Example 2 was added to the dish, and the dish was gently shaken at room temperature for 1 hour. The silica-coated substrate was taken out from the dish, and then the substrate surface was washed ten times with TBS buffer. The washed silica coated substrate was immersed in TBS buffer again, and the PHA synthetase activity was measured according to the method described in Reference Example 2. The results of measurement of the PHA synthetase activity are shown in Table 8.

TABLE 8

Enzyme activity of each PHA synthetase protein bonded on SBA-15 coated layer

| PHA synthetase | Enzyme activity U |
|---|---|
| 01-YN2-C1(cb) | 0.12 |
| YN2-C1 | 0.005 |

It was shown that the substrate bearing the enzyme protein 01-YN2-C1 having the SBA-15-binding peptide at the N-terminus had high enzyme activity compared with the control substrate bearing enzyme protein YN2-C1, and the enzyme protein 01-YN2-C1 was effectively immobilized on the surface of the silica-coated substrate through the peptide at the N-terminus. This indicates that a fusion comprised of a PHA synthetase as a functional domain 14 and a peptide having an affinity for silicon oxide, fused to the N-terminus of the PHA synthetase as a binding domain 15 can be stably immobilized on a surface coating layer 14 made of silicon oxide through the binding domain 15, and that the PHA synthetase portion corresponding to a functional domain 14 immobilized on the surface retains its original enzyme activity, and can be utilized as a bioreactor.

The PHA synthetase activity of the enzyme protein 01-YN2-C1 immobilized on the silica-coated substrate was measured varying the substrate concentration using the following reaction solutions:

Solution 2: 3'-hydroxyoctanoyl CoA/0.1 M Tris-HCl buffer (pH 8.0) solution, a substrate concentration of 3.0 mM;

Solution 2-1: 3'-hydroxyoctanoyl CoA/0.1 M Tris-HCl buffer (pH 8.0) solution, a substrate concentration of 1.5 mM; and Solution 2-2: 3'-hydroxyoctanoyl CoA/0.1 M Tris-HCl buffer (pH 8.0) solution, a substrate concentration of 6.0 mM. The results of evaluation of the enzyme protein 01-YN2-C1 immobilized on the silica-coated substrate with different substrate concentrations are shown in Table 9.

TABLE 9

Substrate concentration-dependency of PHA synthetase immobilized on SBA-15 coat layer

| Reaction Solution/substrate concentration | Reaction Amount (U) |
|---|---|
| Solution 2-1: 1.5 mM | 0.07 |
| Solution 2: 3.0 mM | 0.16 |
| Solution 2-2: 6.0 mM | 0.29 |

The reaction amount varied depending on the concentration of the substrate 3'-hydroxyoctanoil CoA added in the reaction system, indicating that the enzyme protein 01-YN2-C1 immobilized on the silica coated substrate through the peptide having an affinity for silicon oxide retains its original enzyme activity, and can be utilized as a bioreactor.

Example 6

Figure 2:
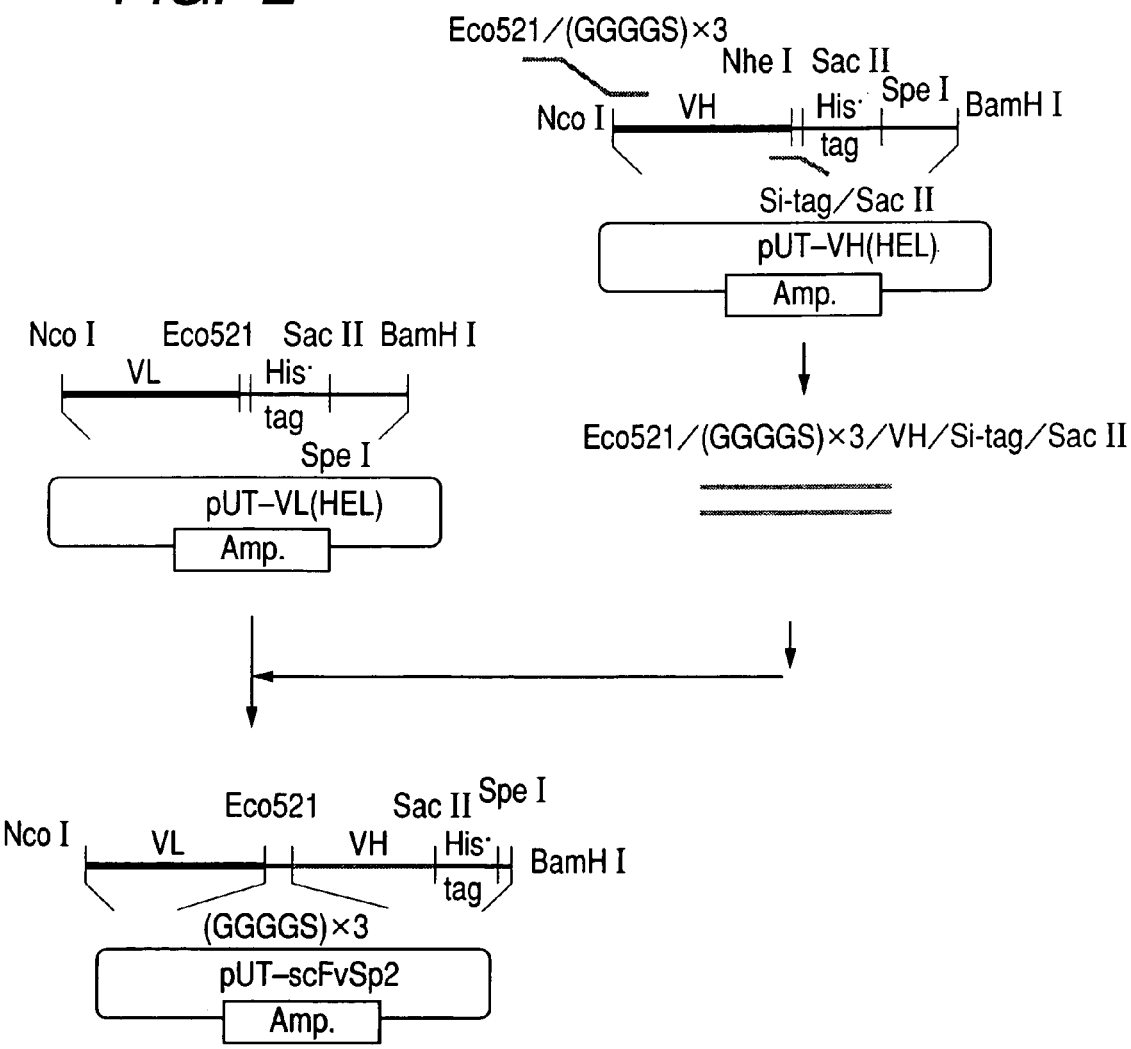
FIG. 2 is a diagram showing a method for production of an expression vector pUT-scFv (HEL).

Preparation of HEL(Hen Egg Lysozyme)-Binding scFv/SBA-15-Binding Peptide Fusion Protein A protein having an SBA-15-binding peptide (SEQ ID NO:IPHVHHKHPHV) fused to HEL binding scFv at the C-terminus is prepared by the following steps.
(1) Preparation of Expression Vector Components of HEL binding scFv, VL (clone name: VL_HEL, SEQ ID NO: 24 and SEQ ID NO: 25) and VH (clone name: VH_HEL, SEQ ID NO: 26 and SEQ ID NO: 27) are respectively inserted into the multi cloning site of pET-15b (Novagen Co., Ltd.) modified as shown in FIG. 2. They are called pUT-VL_HEL and pUT-VH_HEL, respectively.

Then, an expression vector pUT-scFv (HEL) is prepared as follows, which expresses a fusion protein as a sequential translation of VL code gene, linker (GGGGS)×3, VH code gene, GS, SBA-15-binding peptide (SEQ ID NO: 2, IPHVH-HKHPHV) and His×6 (hereinafter referred to as His tag). See FIG. 2.

The following primers are used for PCR with the above pUT-VH_HEL as a template:

SiscFv-B

[SEQ ID NO: 28]
5'-NNNNNNACGGCCGGCGGGGGCGGTAGCGGCGGTGGCGGGTCGGCGGT
GGCGGATCGGATATCCAGCTGCAGGAGT-3';
and SiscFv-F

[SEQ ID NO: 29]
5'-NNNNNCCGCGGGTGGGGGTGCTTGTGGTGCACGTGCATGGGGATGCT
ACCCGCGGAGACGGTGACGAGGGT-3'.

Here, PCR is performed using a commercially available PCR kit (Takara Bio La-Taq Kit) in accordance with a protocol recommended by the provider.

The PCR product obtained is subjected to 2% agarose gel electrophoresis. Then, using a gel extraction kit (Promega Co., Ltd.), PCR fragments of about 400 bp are partially purified. Sequencing is carried out to confirm that it has a desired base sequence. pUT-VL_HEL and the PCR fragment obtained in the above are cut with Eco52I/SacII. Then, agarose electrophoresis is performed to purify the desired vector and insert.

The purified nucleic acid fragments obtained in the above are mixed in a ratio of Vector:Insert=1:5, and ligated in the same manner as in Example 1.

Then, 40 μL of JM109 competent cell is transformed with the ligation reaction solution. The transformation is carried out under heat shock conditions of: in ice, then at 42° C. for 90 seconds, and then in ice. 750 μL of LB culture medium is added to the transformation solution, and culture is conducted with shaking at 37° C. for 1 hour. Thereafter, centrifugation is carried out at 6000 rpm for 5 minutes, 650 μL of culture supernatant is discarded, and the remaining supernatant and cell pellet are mixed, spread over an LB/amp agar plate, and left standing at 37° C. overnight.

One colony is randomly selected from the plate, and cultured with shaking in 3 mL of LB/amp liquid culture medium. After that, using a commercially available MiniPrep Kit (manufactured by Promega Co., Ltd.), plasmid was extracted according to the method recommended by the provider. The obtained plasmid is cut using NotI/SacII. Then, agarose gel electrophoresis is carried out to confirm that the desired gene fragment was inserted. This plasmid is determined to be pUT-scFvSp2.
1) Transformation Then, the plasmid pUT-scFvSp2 obtained above is used to transform 40 μL of BL21 (DE3) competent cells. The transformation is carried out under heat shock conditions of: in ice, then at 42° C. for 90 seconds, and then in ice. 750 μL of LB culture medium is added to the above transformed BL21 solution, and culture is conducted with shaking at 37° C. for 1 hour. Thereafter, centrifugation is carried out at 6000 rpm for 5 minutes, 650 μL of supernatant is discarded, and the remaining supernatant and cell pellet are stirred, spread over an LB/amp agar plate, and left standing at 37° C. overnight.
2) Preliminary Culture One colony on the plate is randomly selected, and cultured in 3.0 mL of LB/amp at 28° C. overnight.
3) Main Culture The above preliminary culture is used to inoculate 750 ML of 2×YT culture medium, and culture is further continued at 28° C. When OD600 exceeds 0.8, IPTG is added to a final concentration of 1 mM, and culture is further conducted at 28° C. overnight.
4) Purification Desired polypeptide is purified from the insoluble granule fraction by the following steps.
<1> Collection of Insoluble Granules The culture obtained in the above step 3) is centrifuged at 6000 rpm for 30 minutes to obtain cell pellet. The obtained cells are suspended in 15 ml of Tris solution (20 mM Tris/500 mM NaCl) in ice. The obtained suspension is disrupted by using a French press to obtain a cell lysate. Then, the cell lysate is centrifuged at 12,000 rpm for 15 minutes, and the supernatant is discarded to obtain the pellet as the insoluble granule fraction.

<2> Solubilization of Insoluble Granule Fraction 6M of the insoluble fraction obtained in the step <1> is added to 10 mL of a guanidine hydrochloride/Tris solution, and immersed overnight. Then, it is centrifuged at 12,000 rpm for 10 minutes to obtain the supernatant as a solubilization solution.

<3> Metal Chelate Column

His-Bind (manufactured by Novagen Co., Ltd.) is used as a metal chelate column. Column preparation, sample loading and washing steps are carried out at room temperature (20° C.) in accordance with a method recommended by the provider. A desired His tag-fused polypeptide is eluted with a 60 mM imidazole/Tris solution. SDS-PAGE (acryl amide 15%) of the eluate is carried out to confirm that the peptide migrates as a single band, i.e., purified.

<4> Dialysis

The above eluate is dialyzed at 4° C. against a 6M guanidine HCl/Tris solution as an external solution to remove imidazole in the eluate. Thus the desired polypeptide is obtained.

<5> Refolding

A solution of the polypeptide scFv-Sp2 having HEL binding Fv and the above binding peptide is subjected dialysis (4° C.) as follows to remove guanidine HCl for refolding of the protein.

1) With a 6M guanidine HCl/Tris solution, the sample is adjusted to a concentration of 7.5 µM (volume after dilution: 10 ml) based on the molar absorption coefficients and ΔO.D. (280 nm to 320 nm) of the respective polypeptides. Then, β-mercapto ethanol (reducing agent) is added to the sample to a final concentration of 375 µM (50-fold of protein concentration), and the sample is reduced at room temperature in a dark place for 4 hours. This sample solution is put in a dialysis bag (MWCO: 14,000) for dialysis.

2) The dialysis bag is immersed in a dialysis external solution of 6M guanidine HCl/Tris solution, and dialyzed for 6 hours with gentle stirring.

3) The guanidine-HCl concentration of the external solution is stepwise reduced from 6M to 3M and then to 2M. The sample is dialyzed for 6 hours at each concentration.

4) A dialysis solution was prepared by adding to a Tris solution (20 mM tris, 500 mM NaCl), oxidized glutathione (GSSG) to a final concentration 375 µM, L-arginine (Arg) to a final concentration of 0.4 M, and then the 2M external dialysis solution of the above step 3) to a final concentration of 1M guanidine HCl (adjusted to pH 8.0 (4° C.) with NaOH). The sample obtained in the step 3) is dialyzed against this dialysis solution for 12 hours with gentle stirring.

5) A Tris solution containing L-arg and 0.5 M guanidine-HCl is prepared as in step 4), and the sample is further dialyzed for 12 hours.

6) Finally, the sample is dialyzed against a Tris solution (20 mM tris, 500 mM NaCl) for 12 hours.

7) After completion of the dialysis, centrifugal separation is carried out at 10000 rpm for about 20 minutes to remove aggregates from the supernatant.

The obtained supernatant is further dialyzed against a phosphate buffer (hereinafter referred to as PBS). The obtained solution is subjected to affinity purification with HEL-immobilized sepharose.

Example 7

Structure Preparation

<1> 200 mg of SBA-15 prepared in Reference Example 1 is immersed in a 0.1% Tween20/phosphate buffer: PBST (pH 7.4) overnight.

<2> Then, 1.5 µM scFv/PBST fused to the silica-binding peptide prepared in Example 6 is mixed with the above SBA-15, and the mixture is stirred for 24 hours.

<3> Subsequently, the mixture is centrifuged at 12,000 rpm for 5 minutes to collect the precipitate. The precipitate is dried under vacuum to obtain a structure.

Example 8

Test Kit (1)

<1> Three Eppendorf tubes are prepared to contain 0.1, 0.5 and 1 µM of HEL (SEIKAGAKU CORPORATION) in PBST solution respectively.

<2> The structure obtained in Example 7 and the HEL solutions obtained in the above step <1> are mixed together, and the mixtures are left standing at room temperature for 1 hour.

<3> The above reaction solutions are centrifuged (12000 rpm×5 minutes) to collect the precipitating fraction containing the structure. Further, 500 µL of PBST is added to each precipitate, which is stirred for 5 minutes. Centrifugation (12000 rpm×5 minutes) is carried out again, and then the supernatant is discarded. This process is repeated five times.

<4> Then, 100 nM of anti-HEL polyclonal antibodies labeled with FITC is mixed, and each mixture is incubated at room temperature.

<5> The above reaction solution is centrifuged (12000 rpm×5 minutes) to separate a precipitate containing the structure and the supernatant, and the supernatant is discarded. Further, 500 µL of PBST is added to each precipitate, which is stirred for 5 minutes. Centrifugation (12000 rpm×5 minutes) is carried out again, and then the supernatant is discarded. This process is repeated five times.

<6> The precipitates obtained as described above are re-suspended in PBS, and fluorescent measurement is made at 520 nm using a fluorometer.

Comparative Example 1

<1> The porous material SBA-15 obtained in Reference Example 1 and 100 nM of HEL polyclonal antibody are mixed together, and the mixture is incubated at room temperature.

<2> The above reaction solution is centrifuged (12000 rpm×5 minutes) to separate a precipitate containing the structure and the supernatant, and the supernatant is discarded.

<3> Then, 500 µL of PBST is added to the above precipitate section, which is stirred for 5 minutes. Centrifugation (12000 rpm×5 minutes) is carried out again, and then the supernatant is discarded. This process is repeated five times.

<4> The precipitate obtained as described above are re-suspended in PBS, and subjected to fluorescent measurement at 520 nm using a fluorometer.

Difference between the fluorescent measurement values obtained in Example 8 and Comparative Example 1 is used as an index of the HEL-binding amount at each concentration. By plotting the relation between the HEL concentration and the fluorescent intensity, whether linearity is obtained and the structure functions as a sensor are determined.

Example 9

Preparation of HEL-Binding scFv/SBA-15-Binding Peptide Fusion Protein

A protein having an SBA-15-binding peptide IPHVHH-KHPHPR fused to HEL-binding scFv at the C-terminus is prepared by the following steps.
(1) Preparation of Expression Vector Components of HEL binding scFv, VL (clone name: VL_HEL, SEQ ID NO: 24 and SEQ ID NO: 25) and VH (clone name: VH_HEL, SEQ ID NO: 26 and SEQ ID NO: 27) are respectively inserted into the multi cloning site of pET-15b (Novagen Co., Ltd.) modified as shown in FIG. 2. They are called pUT-VL_HEL and pUT-VH_HEL, respectively.

Then, an expression vector pUT-scFv (HEL) is prepared as in Example 6, which expresses a fusion protein as a result of sequential translation of VL code gene, linker (GGGGS)×3, VH code gene, GS, SBA-15-binding peptide (SEQ ID NO: 30, IPMHVHHKHPR) and His×6 (His tag).

The following primers are used to perform PCR with pUT-VH_HEL obtained as described above as a template:

```
SiscFv-B
                                            [SEQ ID NO: 31]
5'-NNNNNACGGCCGGCGGGGCGGTAGCGGCGGTGGCGGGTCGGGCGGT GGCGGATCGGATATCCAGCTGCAGGAGT-3';
and SiscFv-F
                                            [SEQ ID NO: 32]
5'-NNNNNCCGCGGGTGGTGCTTGTGGTGCACGTGCATGGGGATGCTACC

CGCGGAGACGGTGACGAGGGT-3'.
```

Then, a fusion of SBA-15-binding peptide (SEQ ID NO: 30, IPMHVHHKHPR) and HEL-binding scFv is obtained in the same manner as in Example 6.

Example 10

Preparation of HEL-Binding scFv/SBA-15-Binding Peptide Fusion Protein (2)

A fusion protein was prepared in the same manner as in Example 6 except that a peptide having affinity to SBA-15 (SEQ ID NO:33, IPMHVHRHPHV, a variant of SEQ ID NO:2) was fused to C-terminus of HEL-binding Fv by the following steps.
(1) Construction of Expression Vector An expression vector for a fusion protein is constructed in the same manner as in Example 6, except that a synthetic DNA encoding the peptide of SEQ ID 33 is used. Using this expression vector, a fusion protein where SBA-15-affinity peptide (SEQ ID NO:33) is fused to the C terminus of HEL-binding scFv protein is obtained as a PBS solution.

To synthesize dsDNA encoding a linker sequence (GGGGS)×3, VH (SEQ ID NO:26), GS linker and SBA-15-affinity peptide (SEQ ID NO: 33), the following primers are used in PCR:

```
SiscFV-B2
                                            (SEQ ID NO: 31)
5'-NNNNNACGGC CGGCGGGGGC GGTAGCGGCG GTGGCGGGTC GGGCGGTGGC GGATCGGATA TCCAGCTGCAGGAGT 3',
and SiscFv-F3
                                            (SEQ ID NO:34)
5'-NNNNNGACGT GGGGGTGCCT GTGGTGCACG TGCATGGGGA

TGCTACCCGC GGAGACGGTG ACGAGGGT 3'.
```

The forward primer SiscFV-B2 (SEQ ID NO:31) contains in its 5' end a base sequence encoding a linker sequence (GGGS)×3, and the reverse primer SiscFv-F3 (SEQ ID NO:34) contains at its 5' end a sequence complementary to a sequence encoding spacer GS and SBA-affinity peptide IPMHVHHRHPR (SEQ ID NO:33).

Example 11

Preparation of HEL-Binding scFv/SBA-15-Binding Peptide Fusion Protein (3)

A fusion protein was prepared in the same manner as in Example 6 except that a peptide having affinity to SBA-15 (SEQ ID NO:35, IPMRVHHKHPHV, a variant of SEQ ID NO:2) was fused to C-terminus of HEL-binding Fv by the following steps.
(1) Construction of Expression Vector An expression vector for a fusion protein is constructed in the same manner as in Example 6, except a synthetic DNA encoding the peptide of SEQ ID 35 is used. Using this expression vector, a fusion protein where SBA-15-affinity peptide (SEQ ID NO:35) is fused to the C terminus of HEL-binding scFv protein is obtained as a PBS solution.

To synthesize dsDNA containing a base sequence encoding a linker sequence (GGGGS)×3, VH (SEQ ID NO:26), GS linker, SBA-15-affinity peptide (SEQ ID NO: 35), the following primers are used in PCR:

```
SiscFV-B2
                                            (SEQ ID NO: 31)
5'-NNNNNACGGC CGGCGGGGGC GGTAGCGGCG GTGGCGGGTC GGGCGGTGGC GGATCGGATA TCCAGCTGCAGGAGT 3',
and SiscFv-F4
                                            (SEQ ID NO: 36)
5'-NNNNNGACGT GGGGGTGCTT GTGGTGCACT CTCATGGGGA

TGCTACCCGC GGAGACGGTG ACGAGGGT-3'.
```

The forward primer SiscFV-B2 (SEQ ID NO:31) contains in its 5' end a base sequence complementary encoding a linker sequence (GGGS)×3, and the reverse primer SiscFv-F3 (SEQ ID NO:36) contains at its 5' end a base sequence complementary a base sequence encoding spacer GS and SBA-affinity peptide IPMRVHHKHPR (SEQ ID NO:35).

Example 12

HEL-Detection Kit

Three fusion proteins are prepared by fusing three SBA-affinity peptides: SEQ ID NO:30 (IPMHVHHKHPR), NO:33 (IPMHVHHRHPHV), and NO:35 (IPMRVHHKHPHV) to the C-terminus of HEL-binding scFv protein respectively, according to Example 11 or 12. These fusion constructs are bound to the surface of the porous body SBA-15 according to Example 7.

Next, the feasibility of a combination of a primary antibody for binding/immobilizing the target HEL and a secondary antibody for detection as a quantitative test kit for the target HEL is validated, where the primary antibody is the fusion protein of HEL-binding scFv protein and silica-affinity peptide immobilized on the surface the structure prepared according to the procedure in Example 8, and the secondary antibody is the FITC-labeled anti-HEL polyclonal antibody.

It should be noted that there is no detectable difference in the density of the immobilized fusion protein on the surface of the structures between the four fusion proteins fused to SBA-15 affinity peptides of SEQ ID NOs: 30, 33, 35 and 2 respectively. That is, no difference is detected in the binding ability to the surface of SBA-15 between SBA-affinity peptide of SEQ ID NO:2 and other three variant affinity peptides, i.e., SEQ ID NOS: 30, 33 and 35.

INDUSTRIAL APPLICABILITY

The present invention provides an organic material-immobilizing structure, for example, a substrate having a biomaterial immobilized on the surface, wherein a silicon oxide layer is provided as the substrate surface on which the biomaterial is to be immobilized, and the organic material to be immobilized comprises a binding domain that enables binding to the above-described silicon oxide layer and a functional domain being the biomaterial itself to which the binding domain is fused, whereby biomaterial portion can be selectively immobilized to the substrate via the binding domain without directly contacting the substrate surface. The function of the biomaterial immobilized on the substrate surface through the independently provided binding domain is not affected by immobilization, and is not chemically affected because no reagents are used in the immobilization. Thus, in the biomaterial-immobilizing substrate obtained according to the present invention, the biomaterial is immobilized on the substrate surface efficiently and with high orientation with minimal influence on its functions.

That is, the present invention is applicable to improve the performance of products utilizing function of various biomaterials, including biosensors and bioreactors that utilize various physiological functions of the organic material or biomaterial immobilized on the substrate surface.

This application claims priority from Japanese Patent Application Nos. 2003-295476 filed Aug. 19, 2003 and 2004-220170 filed Jul. 28, 2004, both of which are hereby incorporated by reference herein.

The invention claimed is:

1. A structure having an organic material immobilized on the surface of a substrate, wherein:
   at least a part of the surface of the substrate comprises one or more members containing a silicon oxide,
   the organic material is bound to the surface of the substrate through a binding domain containing at least a peptide comprising an amino acid sequence capable of binding to the silicon oxide,
   the silicon oxide is mesoporous silica SBA-15, and
   the peptide comprises:
   at least one amino acid sequence selected from the group consisting of the following amino acid sequences:
   Val-Ser-Pro-Met-Arg-Ser-Ala-Thr-Thr-His-Thr-Val (SEQ ID NO: 1); and
   Ile-Pro-Met-His-Val-His-His-Lys-His-Pro-His-Val (SEQ ID NO: 2); or
   a repeating structure of the at least one amino acid sequence.

2. The structure according to claim 1, wherein the organic material is a biomaterial.

3. The structure according to claim 2, wherein a linker comprising one or more amino acids is present in a linking portion between the biomaterial and the peptide in the binding domain.

4. The structure according to claim 1, wherein at least a part of the substrate is porous.

5. A method for production of a structure having an organic material immobilized on the surface of a substrate comprising the steps of:
   obtaining a fusion of the organic material and a binding domain containing at least a peptide comprising an amino acid sequence capable of binding to a silicon oxide by linking the organic material to the binding domain; and
   binding at least a part of the binding domain to the surface of the substrate, the surface comprising at least one member containing the silicon oxide, thereby immobilizing the organic material on the surface of the substrate through the binding domain,
   wherein the silicon oxide is mesoporous silica SBA-15, and
   wherein the peptide comprises:
   at least one amino acid sequence selected from the group consisting of the following amino acid sequences:
   Val-Ser-Pro-Met-Arg-Ser-Ala-Thr-Thr-His-Thr-Val (SEQ ID NO: 1); and
   Ile-Pro-Met-His-Val-His-His-Lys-His-Pro-His-Val (SEQ ID NO: 2); or
   a repeating structure of the at least one amino acid sequence.

6. A peptide having an affinity for silicon oxide, the silicon oxide being mesoporous silica SBA-15,
   the peptide comprising:
   at least one amino acid sequence selected from the group consisting of the following amino acid sequences:
   Val-Ser-Pro-Met-Arg-Ser-Ala-Thr-Thr-His-Thr-Val (SEQ ID NO: 1); and
   Ile-Pro-Met-His-Val-His-His-Lys-His-Pro-His-Val (SEQ ID NO: 2); or
   a repeating structure of the at least one amino acid sequence.

7. A DNA encoding a peptide having an affinity for a silicon oxide, the silicon oxide being mesoporous silica SBA-15,
   the peptide comprising:
   at least one amino acid sequence selected from the group consisting of the following amino acid sequences:
   Val-Ser-Pro-Met-Arg-Ser-Ala-Thr-Thr-His-Thr-Val (SEQ ID NO: 1); and
   Ile-Pro-Met-His-Val-His-His-Lys-His-Pro-His-Val (SEQ ID NO: 2); or
   a repeating structure of the at least one amino acid sequence,
   wherein the DNA comprises a base sequence encoding the peptide.

8. A vector including a DNA encoding a peptide having an affinity for silicon oxide,
   wherein the silicon oxide is mesoporous silica SBA-15,
   wherein the peptide comprises:
   at least one amino acid sequence selected from the group consisting of the following amino acid sequences:

Val-Ser-Pro-Met-Arg-Ser-Ala-Thr-Thr-His-Thr-Val (SEQ ID NO: 1); and

Ile-Pro-Met-His-Val-His-His-Lys-His-Pro-His-Val (SEQ ID NO: 2); or a repeating structure of the at least one amino acid sequence, and wherein the DNA comprises a base sequence encoding the peptide.

9. A detector for detecting a target substance in a sample comprising:

means for contacting a structure having an organic material immobilized on the surface of a substrate according to claim 1 with a sample whereby the organic material is bound to the target substance in the sample; and means for detecting the bound target substance.

10. A detection method for detecting a target substance in a sample, comprising the steps of:

contacting a structure having an organic material immobilized on the surface of a substrate according to claim 1 with the sample to bind the organic material to the target substance of the specimen; and detecting the bound target substance.

* * * * *